(12) United States Patent
Furneaux et al.

(10) Patent No.: US 7,098,334 B2
(45) Date of Patent: Aug. 29, 2006

(54) 4-AMINO-5H-PYRROLO[3,2-D]PYRIMIDINE INHIBITORS OF NUCLEOSIDE PHOSPHORYLASES AND NUCLEOSIDASES

(75) Inventors: Richard Hubert Furneaux, Wellington (NZ); Peter Charles Tyler, Wellington (NZ); Vern L. Schramm, New Rochelle, NY (US); Gary Brian Evans, Lower Hutt (NZ)

(73) Assignees: Industrial Research Limited, Auckland (NZ); Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 10/395,636

(22) Filed: Mar. 24, 2003

(65) Prior Publication Data

US 2004/0110772 A1 Jun. 10, 2004

(30) Foreign Application Priority Data

Mar. 25, 2002 (NZ) ...................... 517970

(51) Int. Cl.
C07D 487/04 (2006.01)
(52) U.S. Cl. .................................... 544/280
(58) Field of Classification Search ........... 514/264.11; 544/280
See application file for complete search history.

(56) References Cited

U.S. PATENT DOCUMENTS

| | | | |
|---|---|---|---|
| 5,985,848 | A | 11/1999 | Furneaux et al. |
| 6,066,722 | A | 5/2000 | Furneaux et al. |
| 6,228,847 | B1 | 5/2001 | Furneaux et al. |
| 6,379,911 | B1 | 4/2002 | Schramm et al. |
| 6,458,799 | B1 | 10/2002 | Montgomery et al. |
| 6,492,347 | B1 | 12/2002 | Furneaux et al. |
| 6,693,193 | B1 | 2/2004 | Furneaux et al. |
| 6,764,829 | B1 | 7/2004 | Schramm et al. |
| 6,803,455 | B1 | 10/2004 | Furneaux et al. |
| 2004/0053944 | A1 | 3/2004 | Furneaux et al. |
| 2004/0181063 | A1 | 9/2004 | Furneaux et al. |

FOREIGN PATENT DOCUMENTS

| WO | WO 99/19338 | 4/1999 |
|---|---|---|
| WO | WO 02/18371 A1 | 3/2002 |

OTHER PUBLICATIONS

Wolff, Manfred E. "Burger's Medicinal Chemistry, 5ed, Part I", John Wiley & Sons, 1995, pp. 975-977.*

Banker, G.S. et al, "Modern Pharmaceutics, 3ed.", Marcel Dekker, New York, 1996, pp. 451 and 596.*

Tang B, Li YN, Kruger WD, Cancer Res. Oct. 1, 2000;60(19):5543-7.*

Draetta, G. and Pagano, M. in "Annual Reports in Medicinal Chemistry, vol. 31", 1996, Academic Press, San Diego, p. 241-246.*

Evans et al., entitled "8-Aza-immucillins as Transition-State Analogue Inhibitors of Purine Nucleoside Phosphorylase and Nucleoside Hydrolases," J. Med. Chem., 46, pp. 155-160, 2003.

Kicska et al,, entitled "Purine-less Death in Plasmodium falciparium Induced by Immucillin-H, a Transition State Analogue of Purine Nucleotide Phosphorylase," The Journal of Biological Chemistry, vol. 277, No. 5, Issue of Feb. 1, pp. 3226-3231, 2002.

Evans GB, et al., entitled "Targeting the Polyamine Pathway with Transition-State Analogue Inhibitors of 5'-Methylthioadenosine Phosphorylase," J. Med. Chem. 2004, 47, 3275-3281.

* cited by examiner

Primary Examiner—Thomas C. McKenzie
(74) Attorney, Agent, or Firm—Amster, Rothstein & Ebenstein LLP

(57) ABSTRACT

The invention provides a compound of the formula:

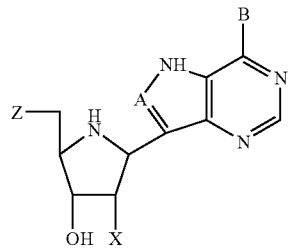

wherein A is selected from N, CH and CR; R is selected from halogen, optionally substituted alkyl, aralkyl and aryl, OH, $NH_2$, $NHR^1$, $NR^1R^2$ and $SR^3$; $R^1$, $R^2$ and $R^3$ are each optionally substituted alkyl, aralkyl or aryl groups; B is selected from $NH_2$ and $NHR^4$; $R^4$ is an optionally substituted alkyl, aralkyl or aryl group; X is selected from H, OH and halogen; Z is selected from H, Q, SQ and OQ; Q is an optionally substituted alkyl, aralkyl or aryl group; or a tautomer, a pharmaceutically acceptable salt, an ester, or a prodrug thereof; with the proviso that the stereochemistry of the aza-sugar moiety is D-ribo or 2'-deoxy-D-erythro-; pharmaceutical compositions comprising said compound; and methods of treatment using said compound.

16 Claims, 3 Drawing Sheets

4-AMINO-5H-PYRROLO[3,2-D]PYRIMIDINE INHIBITORS OF NUCLEOSIDE PHOSPHORYLASES AND NUCLEOSIDASES

STATEMENT OF GOVERNMENT SUPPORT

The invention disclosed herein was made with U.S. Government support under grant number GM41916 from the National Institutes of Health, U.S. Department of Health and Human Services. Accordingly, the U.S. Government has certain rights in this invention.

This application claims priority to New Zealand Application No. 517970, filed Mar. 25, 2002.

TECHNICAL FIELD

This invention relates to certain nucleoside analogues which are inhibitors of 5'-methylthioadenosine phosphorylases and 5'-methylthioadenosine nucleosidases, processes for preparing these compounds, their use in the treatment of diseases and infections, and pharmaceutical compositions containing them.

BACKGROUND

U.S. Pat. No. 5,985,848, U.S. Pat. No. 6,066,722 and U.S. Pat. No. 6,228,741 are directed to nucleoside analogues that are inhibitors of purine nucleoside phosphorylase (PNP). The analogues are useful in treating parasitic infections, as well as T-cell malignancies and autoimmune diseases.

PCT/NZ00/00048 provides a process for preparing these PNP inhibitor compounds. This application recognises the compounds as PNP inhibitors and addresses a need for simpler methods of preparing them.

PNP catalyses the phosphorolytic cleavage of ribo- and deoxyribonucleosides, for example those of guanine and hypoxanthine, to give the corresponding sugar-1-phosphate and guanine, hypoxanthine or other purine bases.

The applicants have now determined that certain of these PNP inhibitor compounds are actually powerful and biologically available inhibitors of 5'-methylthioadenosine phosphorylase (MTAP) and 5'-methylthioadenosine nucleosidase (MTAN).

MTAP and MTAN function at or near the crossroads of polyamine biosynthesis, and of purine salvage in mammals and microbes, and of quorum sensing pathways in microbes. They respectively catalyse the reversible phosphorolysis of 5'-methylthioadenosine (MTA) to adenine and 5-methylthio-$\alpha$-D-ribose-1-phosphate (MTR-1P), and the hydrolysis of MTA to adenine and 5-methylthio-$\alpha$-D-ribose. The adenine formed is subsequently recycled, converted into nucleotides and is essentially the only source of free adenine in the human cell. The MTR-1P is subsequently converted into methionine by successive enzymatic actions.

Scheme 1 shows the role of MTAP and MTA in polyamine biosynthesis. Scheme 2 shows the reaction catalysed by MTAP (phosphorolysis of MTA to adenine and 5-methylthio-$\alpha$-D-ribose-1-phosphate) including the proposed transition state structure.

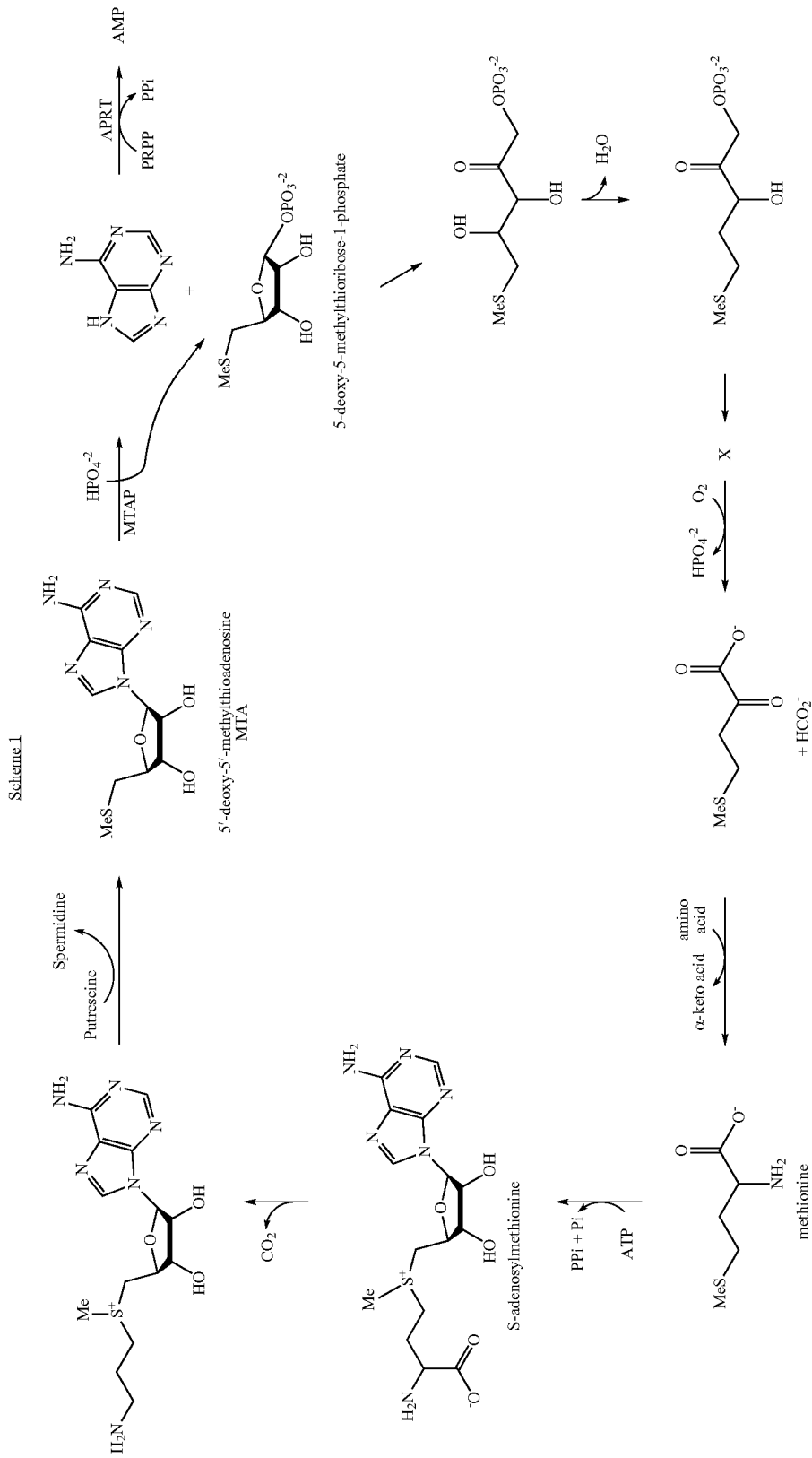

Scheme 2

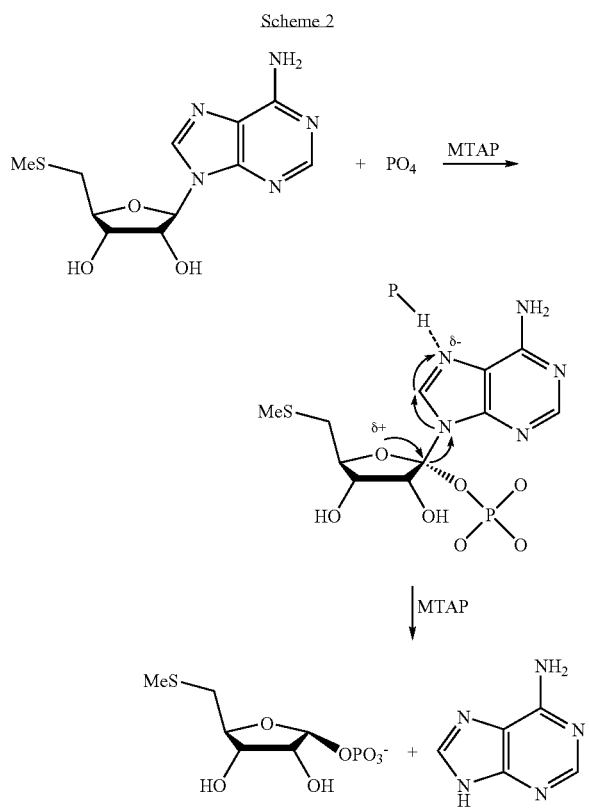

MTA is a by-product of the reaction involving the transfer of an aminopropyl group from decarboxylated S-adenosyl methionine to putrescine during the formation of spermidine. The reaction is catalyzed by spermidine synthase. The spermidine synthase is very sensitive to product inhibition by MTA, therefore inhibition of MTAP or MTAN will severely limit the polyamine biosynthesis and the salvage pathway for adenine in the cells.

Inhibition of MTAN may also decrease production of the quorum sensing pathways in bacteria, and thereby decrease the virulence of microbial infections.

In the Al-1 quorum sensing pathway, S-adenosylmethionine (SAM) and specific acyl-acyl carrier proteins are the substrates for homoserine lactone (HSL) biosynthesis. The biosynthesis of HSL results in concomitant release of MTA. Thus, a buildup of MTA due to inhibition of MTAN should result in inhibition of the Al-1 pathway.

In the Al-2 quorum sensing pathway, SAM is converted to S-adenosylhomocysteine (SAH), then to S-ribosylhomocysteine, and on via 4,5-dihydroxy-2,3-pentanedione to the Al-2 quorum sensing molecule. The SAH is a substrate for MTAN, so inhibition of MTAN should directly inhibit the Al-2 pathway.

MTAP deficiency due to a genetic deletion has been reported with many malignancies. The loss of MTAP enzyme function in these cells is known to be due to homozygous deletions on chromosome 9 of the closely linked MTAP and p16/MTS1 tumour suppressor gene. As absence of p16/MTS1 is probably responsible for the tumour, the lack of MTAP activity is a consequence of the genetic deletion and is not causative for the cancer. However, the absence of MTAP alters the purine metabolism in these cells so that they are mainly dependent on the de novo pathway for their supply of purines. That makes these cells unusually sensitive to inhibitors like methotrexate and azaserine, that block the de novo pathway. Therefore, a combination therapy of methotrexate or azaserine with an MTAP inhibitor will have unusually effective anti-tumour properties.

MTAP inhibitors are may also be effective as radiation sensitizing agents. The inhibition of MTAP could result in a reduced ability to repair damage caused by ionising radiation.

MTAP inhibitors would also be effective against parasitic infection such as malaria that infects red blood cells (RBCs). It has been shown that *Plasmodium falciparum* has an active MTAP pathway (Sufrin, J. R., Meshnick, S. R., Spiess, A. J., Garofolo-Hannan, J., Pan, X- Q. and Bacchi, C. Y. (1995) *Antimicrobial Agents and Chemotherapy*, 2511–2515). This is a target for MTAP inhibitors. Such inhibitors may also kill the parasites without having any negative effect on the host RBCs, as RBCs are terminally differentiated cells and they do not synthesize purines, produce polyamines or multiply.

The polyamine pathway is important in cancer development, and blocking the polyamine pathway with inhibitors of MTAP is expected to provide reduced growth of cancers. Genetically modified mice (TRAMP mice, Gupta, S., Ahmad, N., Marengo, S. R., MacLennan, G. T., Greenberg, N. M., Mukhtar, H. (2000) *Cancer Res.* 60, 5125–5133) with a propensity for prostate tumor development have been described. Treatment of these mice with known inhibitors of the polyamine pathway such as α-difluoromethylornithine (DFMO) delay the onset of cancers and prevent metastasis to other tissues. However, the use of DFMO in humans is limited by its ototoxicity (causes deafness). MTAP inhibitors target a different step in the polyamine pathway, and are also expected to reduce cancer development. Since MTAP inhibitors influence a different step in the pathway, one that is only used in the polyamine pathway in humans, they may act without the side-effects that have limited the application of other polyamine pathway inhibitors.

It is an object of the present invention to provide compounds that are inhibitors of MTAP and/or MTAN, or at least to provide the public with a useful choice.

STATEMENTS OF INVENTION

Accordingly, in a first aspect, the present invention provides a compound of the formula (I):

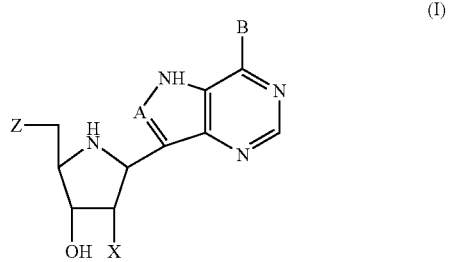

(I)

wherein:
A is selected from N, CH and CR,
where R is selected from halogen, optionally substituted alkyl, aralkyl and aryl, OH, $NH_2$, $NHR^1$, $NR^1R^2$ and $SR^3$,
where $R^1$, $R^2$ and $R^3$ are each optionally substituted alkyl, aralkyl or aryl groups;

B is selected from $NH_2$ and $NHR^4$,
  where $R^4$ is an optionally substituted alkyl, aralkyl or aryl group;
X is selected from H, OH and halogen; and
Z is selected from H, Q, SQ and OQ,
  where Q is an optionally substituted alkyl, aralkyl or aryl group;

or a tautomer thereof; or a pharmaceutically acceptable salt thereof; or an ester thereof; or a prodrug thereof;

with the proviso that the stereochemistry of the aza-sugar moiety is D-ribo or 2'-deoxy-D-erythro-.

Preferably, A is CH. More preferably Z is SQ when A is CH.

It is also preferred that B is $NH_2$. More preferably Z is SQ when B is $NH_2$. Still more preferably Q is $C_1$–$C_5$ alkyl when B is $NH_2$ and Z is SQ.

It is further preferred that A is N. More preferably Z is SQ when A is N. Still more preferably Q is $C_1$–$C_5$ alkyl when A is N and Z is SQ.

Preferably X is OH.

It is also preferred that Z is SQ. More preferably Q is $C_1$–$C_5$ alkyl when Z is SQ. Still more preferably Q is an optionally substituted aryl group when Z is SQ.

Preferred compounds of the invention include those where Q is selected from phenyl, 3-chlorophenyl, 4-chlorophenyl, 4-fluorophenyl, 3-methylphenyl, 4-methylphenyl, benzyl, hydroxyethyl, fluoroethyl, naphthyl, methyl and ethyl, when Z is SQ.

Most preferred compounds of the invention include:
  (1S)-1-(9-deazaadenin-9-yl)-1,4-dideoxy-1,4-imino-5-methylthio-D-ribitol;
  (1S)-1-(9-deazaadenin-9-yl)-1,4,5-trideoxy-1,4-imino-D-ribitol;
  (1S)-1-(9-deazaadenin-9-yl)-1,4-dideoxy-1,4-imino-5-O-methyl-D-ribitol;
  (1S)-1-(7-amino-1H-pyrazolo[4,3-d]pyrimidin-3-yl)-1,4-dideoxy-1,4-imino-5-methylthio-D-ribitol;
  (1S)-1-(9-deazaadenin-9-yl)-1,4-dideoxy-5-ethylthio-1,4-imino-D-ribitol;
  (1S)-1-(9-deazaadenin-9-yl)-1,4-dideoxy-1,4-imino-5-phenylthio-D-ribitol;
  (1S)-1-(9-deazaadenin-9-yl)-5-benzylthio-1,4-dideoxy-1,4-imino-D-ribitol;
  (1S)-1-(9-deazaadenin-9-yl)-1,4-dideoxy-5-(2-hydroxyethyl)thio-1,4-imino-D-ribitol;
  (1S)-1-(9-deazaadenin-9-yl)-1,4-dideoxy-1,4-imino-5-(4-methylphenyl)thio-D-ribitol;
  (1S)-1-(9-deazaadenin-9-yl)-1,4-dideoxy-1,4-imino-5-(3-methylphenyl)thio-D-ribitol;
  (1S)-1-(9-Deazaadenin-9-yl)-5-(4-chlorophenyl)thio-1,4-dideoxy-1,4-imino-D-ribitol;
  (1S)-1-(9-deazaadenin-9-yl)-5-(3-chlorophenyl)thio-1,4-dideoxy-1,4-imino-D-ribitol;
  (1S)-1-(9-deazaadenin-9-yl)-1,4-dideoxy-5-(4-fluorophenyl)thio-1,4-imino-D-ribitol;
  (1S)-1-(9-deazaadenin-9-yl)-1,4-dideoxy-1,4-imino-5-(1-naphthyl)thio-D-ribitol;
  (1S)-1-(9-deazaadenin-9-yl)-1,4-dideoxy-5-(2-fluoroethyl)thio-1,4-imino-D-ribitol; and
  (1S)-1-(9-deazaadenin-9-yl)-1,4,5-trideoxy-5-ethyl-1,4-imino-D-ribitol.

In a second aspect, the invention provides a pharmaceutical composition comprising a pharmaceutically effective amount of a compound of formula (I).

In another aspect, the invention provides a method of treating a disease or condition in which it is desirable to inhibit MTAP, comprising administering a pharmaceutically effective amount of a compound of formula (I) to a patient requiring treatment. The disease includes cancer or a protozoan parasitic infection, such as malaria.

The invention further provides the use of a compound of formula (I) in the manufacture of a medicament for treating a disease or condition in which it is desirable to inhibit MTAP.

In another aspect, the invention provides a method of treating a disease or condition in which it is desirable to inhibit MTAN, comprising administering a pharmaceutically effective amount of a compound of formula (I) to a patient requiring treatment. The disease includes a bacterial infection.

The invention further provides the use of a compound of formula (I) in the manufacture of a medicament for treating a disease or condition in which it is desirable to inhibit MTAN.

DETAILED DESCRIPTION OF THE INVENTION

Figure 1:
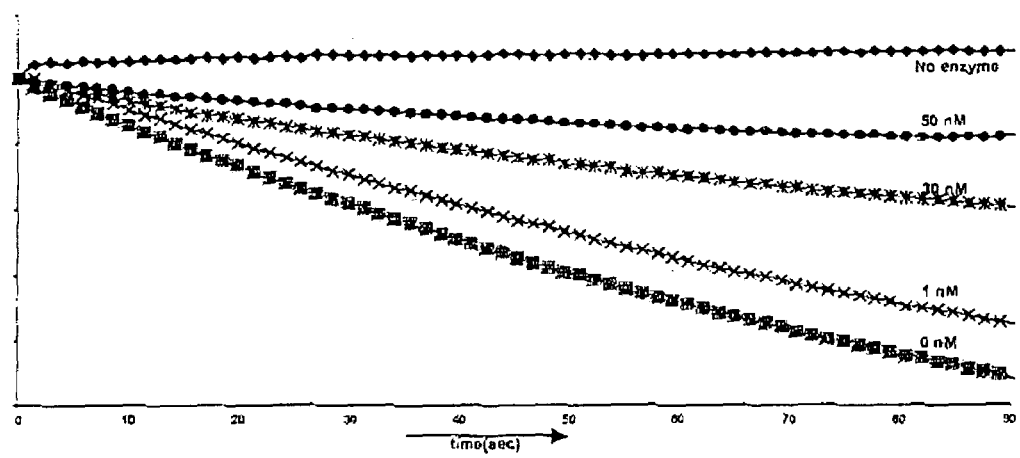
FIG. 1 shows the inhibition of MTAP by 5'-methylthio-ImmA at varying concentrations. (MTA at 150 µM; $K_m$=2.5 µM, $K_i$=107 pM).

This invention provides compounds of the formula (I) as defined above, which are potent inhibitors of MTAP and MTAN. The compounds of the invention are therefore expected to have clinical utility in treating diseases such as cancer, bacterial infections and protozoan parasitic infections (such as malaria).

The compounds of the invention are useful in both free base form and in the form of salts. The term "pharmaceutically acceptable salts" is intended to include non-toxic salts derived from inorganic or organic acids, including, for example, the following acids: hydrochloric, sulfuric, phosphoric, acetic, lactic, fumaric, succinic, tartaric, gluconic, citric, methanesulfonic and p-toluenesulfonic acids.

As used herein, the term "aza-sugar moiety" means a fragment of general structure:

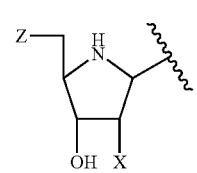

where Z and X are as defined above for a compound of formula (I).

General synthetic methods for preparing the compounds of the invention are given below.

Method (A):

(5'-thio-Immucillin-A derivatives) reacting a compound of formula (II)

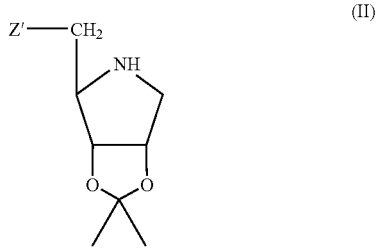
(II)

[wherein Z' is a trialkylsilyloxy, alkyldiarylsilyloxy or optionally substituted triarylmethoxy group]

(typically Z' is a tert-butyldimethylsilyloxy, trityloxy or similar group)

sequentially with N-chlorosuccinimide then a sterically hindered base (such as lithium tetramethylpiperadide) to form an imine, then with the anion of acetonitrile (typically made by treatment of acetonitrile with n-butyllithium). The resulting 3,6-dideoxy-3,6-iminoheptononitrile derivative is then 7-O-deprotected. In the case of a trialkylsilyl or alkyldiarylsilyl protecting group, this is typically achieved by treatment with a fluoride ion source, conveniently tetrabutylammonium fluoride in tetrahydrofuran. In the case of an optionally substituted triarylmethyl protecting group this is typically achieved by use of an acidic reagent, typically boron trifluoride in methanol, or aqueous acetic acid. The resulting 7-hydroxy-derivative is then N-protected by reaction with di-tert-butyl dicarbonate to generate the compound of formula (III)

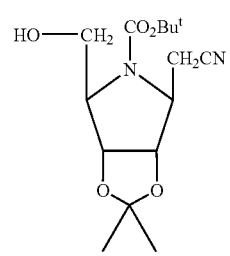
(III)

which is then elaborated by displacement of the 7-hydroxy group, conveniently by sulfonate displacement with a thiolate anion, for example by conversion first to a 7-O-methanesulfonate with methanesulfonyl chloride and base (e.g. triethylamine) and displacement with sodium methanethiolate (e.g. NaSMe in dimethylformamide), to give a compound of formula (IV)

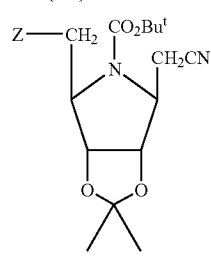
(IV)

[wherein Z is SQ as defined for formula (I)]

which is then elaborated either by condensation with ethyl formate in the prescence of a base, typically sodium hydride, or by condensation with $(Me_2N)_2CHOBu^t$ (Brederek's reagent) and hydrolysis under weakly acidic conditions, to give a compound of formula (V)

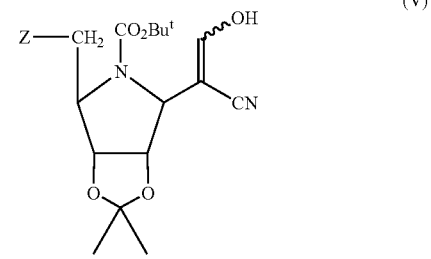
(V)

[wherein Z is SQ as defined for formula (I)]

which is then reacted with aminoacetonitrile under mildly basic conditions, and cyclized by reaction with a simple ester of chloroformic acid (typically benzyl chloroformate or methyl chloroformate) to give a compound of formula (VI)

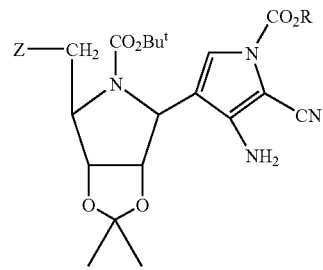
(VI)

[wherein Z is SQ as defined for formula (I) and R is an alkyl or aralkyl group]

which is then deprotected on the pyrrole nitrogen by hydrogenolysis in the presence of a noble metal catalyst (e.g. Pd/C) in the case of a benzyl group or under mildly basic conditions in the case of a simple alkyl group such as a methyl group, and then condensed with formamidine acetate to give a compound of formula (VII)

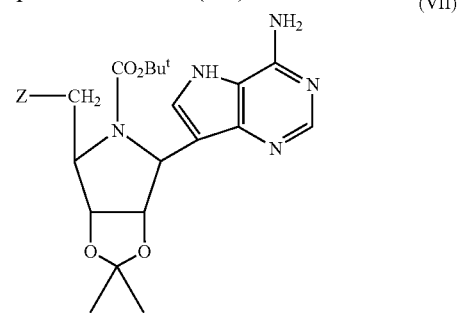
(VII)

[wherein Z is SQ as defined for formula (I)]

which is then fully deprotected under acidic conditions, e.g. by treatment with trifluoroacetic acid or with hydrochloric acid in methanol.

This method follows the approach used to prepare 9-deazaadenosine and its analogues [Lim and Klein, Tetrahedron Lett., 22 (1981) 25, and Xiang et al., Nucleosides Nucleotides 15 (1996) 1821], including Immucillin-A [Evans et al., Tetrahedron 56 (2000) 3053].

Methods for the preparation of a compound of formula (II) [wherein Z' is a tert-butyldimethylsilyloxy group] are detailed in Furneaux et al., Tetrahedron 53 (1997) 2915 and references therein.

An alternative method of making the compound of formula (III) is described in Preparative Example A.

Method (B):

(5'-O-substituted Immucillin-A derivatives) reacting the compound of formula (III) with an optionally substituted alkylating or aralkylating agent in the presence of a base to give a compound of formula (IV) [wherein Z is OQ as defined for formula (I)]. For methylation, a typical reagent combination would be methyl iodide and sodium hydride in a solvent such as tetrahydrofuran, dimethylsulfoxide or dimethylformamide. The resulting compound of formula (IV) [wherein Z is OQ as defined for formula (I)] is then converted to a compound of formula (I) as described for the corresponding conversion of a compound of formula (IV) in Method A.

Method (C):

(5'-deoxy-Immucillin-A derivatives) 7-deoxygenating the compound of formula (III), then converting the resulting compound of formula (IV) [wherein Z is hydrogen] to a compound of formula (I) as described for the corresponding conversion of a compound of formula (IV) in Method A. Deoxygenation can be achieved by various Barton radical deoxygenation methods, or preferably by formation and dehalogenation of a 7-deoxy-7-halogeno-intermediate. Conveniently this would be the 7-deoxy-7-iodo-derivative, formed by sulfonation of the compound of formula (III), typically with methanesulfonyl chloride and base (e.g. diisopropylethylamine), then displacement of the sulfonate group with a source of halide ion, typically sodium iodide in acetone. Dehalogenation would then be affected either by catalytic hydrogenolysis, typically with hydrogen over a palladium catalyst, or preferably with a radical dehalogenation reagent such as tributyltin hydride in benzene.

Method (D):

(8-aza-5'-thio-Immucillin-A derivatives—Daves' methodology) reacting a compound of formula (II) (as defined where first shown above) sequentially with N-chlorosuccinimide and a hindered base (such as lithium tetramethylpiperidide) to form an imine, then condensing this with the anion produced by abstraction of the bromine or iodine atom from a compound of formula (VIII)

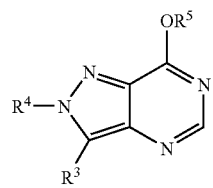

(VIII)

[wherein $R^3$ is a bromine atom, $R^4$ is a tetrahydropyran-2-yl group, and $R^5$ is a methyl group]

typically using butyllithium or magnesium, the coupling preferably being catalyzed by a Lewis acid catalyst, typically tin(IV) chloride at low temperature, typically in the range −30 to −80° C., preferably −78° C., to give a product which is then sequentially (i) N-protected preferably as the tert-butoxycarbonyl derivative, typically by treatment with di-tert-butyl dicarbonate, preferably in methanol at room temperature;

(ii) subjected to a displacement of the methoxy group (introduced as the $R^5O$ of a compound of formula (VIII)) with ammonia, typically with concentrated ammonia in methanol at 100° C.;

(iii) N-protected on the primary amino group, preferably as the N-mono-benzoate, typically by treatment with benzoylimidazole and a catalytic amount of 4-N,N-dimethylaminopyridine in acetonitrile at 65° C.;

(iv) 5'-O-deprotected; in the case of a trialkylsilyloxy or alkyldiarylsilyloxy this is typically achieved by treatment with a fluoride ion source, conveniently tetrabutylammonium fluoride in tetrahydrofuran; in the case of an optionally substituted triarylmethoxy group this is typically achieved by use of an acidic reagent, typically boron trifluoride in methanol, or aqueous acetic acid;

(v) subjected to displacement of the 5'-hydroxy group with thiolacetic acid, preferably under Mitsunobu reaction conditions, typically with a combination of triphenylphosphine and diisopropyl azodicarboxylate in tetrahydrofuran, then thiolacetic acid;

(vi) 5'-S-deprotected then 5'-S-alkylated or 5'-S-aralkylated by sequential reaction with sodium methanethiolate then an alkylating or alkylating agent, conveniently methyl iodide or benzyl bromide in methanol where the 5'-S-methyl or 5'-S-benzyl-derivative is required; and finally (vii) full N,O-deprotection by acidic treatment, conveniently with concentrated aqueous hydrochloric acid in methanol, to give the compound of formula (I) as the dihydrochloride salt.

Methods for preparing compounds of formula (VIII) are described in Stone et al., J. Org. Chem., 44 (1979) 505, and references therein. It will be appreciated that while the tetrahydropyran-2-yl and methyl groups are favoured as the protecting group for this reaction, other O,N-protecting groups can be used.

Method (E):

(5'-alkyl-5'-deoxy-Immucillin derivatives) reacting a compund of formula (X)

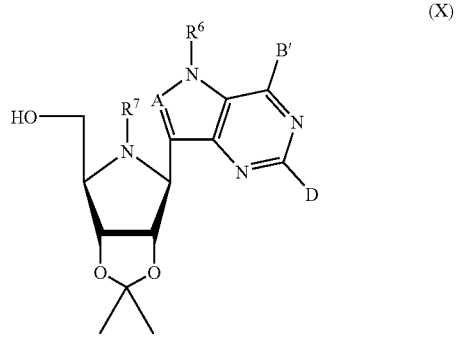

(X)

[wherein $R^6$ is an N-protecting group, $R^7$ is an alkoxycarbonyl or aralkyloxycarbonyl group, B' is selected from $N(R^8)_2$, $R^8$ is an N-protecting group and D is H]

with an oxidizing agent capable to converting the 5'-hydroxy group into a 5'-aldehydo group. There are many such reagents, but conveniently this may be conducted using the Dess-Martin periodinane reagent, or a chromium (VI) oxidant such as Collins reagent ($CrO_3$ in pyridine) or pyridinium dichromate catalyzed by molecular sieves and pyridinium trifluoroacetate;

reacting the resulting aldehyde with a Wittig or Horner-Wittig reagent, chosen depending upon the alkyl substituent required;

hydrogenating the resulting alkene, conveniently using palladium on charcoal as the catalyst;

and finally fully N,O,S-deprotecting the resulting 5'-C-alkyl derivative by acid-, alkali- or fluoride ion-catalyzed hydrolysis or alcoholysis or catalytic hydrogenolysis as required for the O-, N- and S-protecting groups in use.

Compounds of formula (X) can be prepared as described in U.S. Pat. No. 5,985,848.

The N-protecting group $R^6$ in the compound of formula (X) may conveniently be an alkoxymethyl group (such as benzyloxymethyl) or a tetrahydropyranyl group. It will be appreciated that protection of a pyrazolo[4,3-d]primidine moiety can result in one or both of a pair of isomers depending upon which of the nitrogen atoms in the pyrazoles moiety is protected, and that either isomer is satisfactory for the purposes of making a 5'-substituted derivative. The N-protecting group $R^8$ and the S-protecting group $R^9$ in the compound of formula (X) may conveniently be an alkoxymethyl group (such as benzyloxymethyl), a silyl group (such as tert-butyldimethylsilyl) or an arylmethyl group (such as benzyl). Each N-protecting group $R^8$ may conveniently be independently an arylmethyl group (such as benzyl or 4-methoxylbenzyl), or the two $R^8$ groups together may form the 2,4-hexadien-2,5-yl group.

Preparative Method (A):

{Compound (III)}

A compound of formula (III) can be prepared by reacting a compound of formula (II) [as defined where first shown above] with an oxidizing agent, such as meta-chloroperbenzoic acid, or preferably the combination of hydrogen peroxide and selenium dioxide, to give a nitrone of formula (XI)

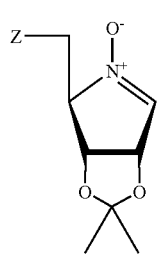

(XI)

[wherein Z is is a trialkylsilyloxy, alkyldiarylsilyloxy or optionally substituted triarylmethoxy group]

which is then reacted in sequence with:

(a) the anion of acetonitrile (typically made by treatment of acetonitrile with n-butyllithium), conveniently in tetrahydrofuran; and (b) a reagent capable of reducing the resulting N-hydroxy group to an amine, conveniently with zinc in acetic acid; and di-tert-butyl dicarbonate, typically in chloroform;

then deprotected at O-5; in the case of a trialkylsilyloxy or alkyldiarylsilyloxy this is typically achieved by treatment with a fluoride ion source, conveniently tetrabutylammonium fluoride in tetrahydrofuran; in the case of an optionally substituted triarylmethoxy group this is typically achieved by use of an acidic reagent, typically boron trifluoride in methanol, or aqueous acetic acid.

Inhibition of MTAP and MTAN

Inhibition constants for selected compounds of the invention are collected in Tables 1 and 2. Table 1 shows inhibition constants for MTAN and Table 2 shows inhibition constants for MTAP.

$K_i$ as shown in Tables 1 and 2 is the initial inhibition constant formed by the enzyme-inhibitor complex, and $K_i^*$ is the equilibrium dissociation constant for inhibition that is observed following a period of slow-onset, tight binding inhibition. Ki* is the biologically effective constant.

The compounds of the invention are potent inhibitors of MTAP and MTAN. For example, 5'-methylthio-ImmA has $K_i^*$ in the pM range for both enzymes. In contrast, methylthio-ImmH, which does not fall within the selected class of compounds, shows no inhibition of MTAN.

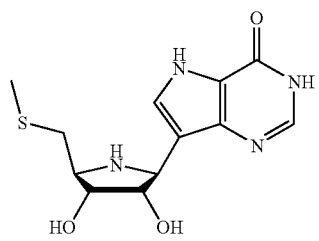

Methylthio-ImmH

Furthermore, Immucillin A, which also does not fall within the selected class of compounds, shows no inhibition of MTAP.

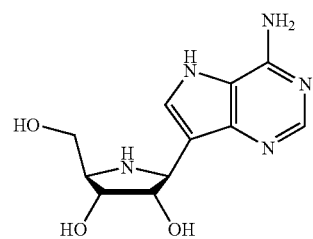

Immucillin-A

TABLE 1

Inhibition Constants for MTAN Inhibitors

| Inhibitor Name | Structure | Ki | Ki* |
| --- | --- | --- | --- |
| 5'-Phenylthio-ImmA | 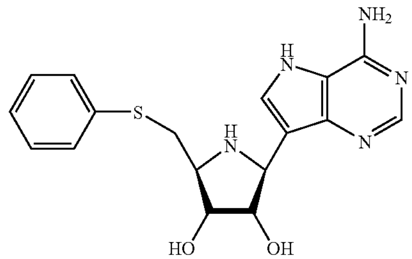 | 46 ± 3 pM | 32 ± 2 pM |
| 5'-methylthio-ImmA | 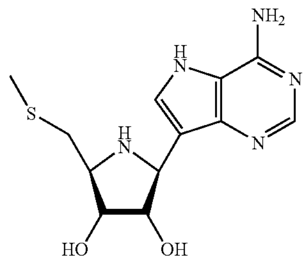 | 130 ± 12 pM | 77 ± 20 pM |
| 5'-Ethylthio-ImmA | 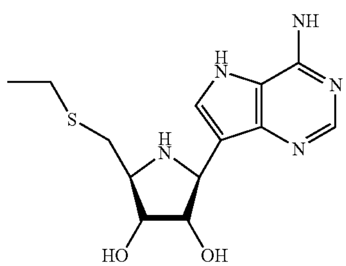 | 73 ± 11 pM | 27 ± 0.3 pM |
| 5'-deoxy-5'-ethyl-ImmA | 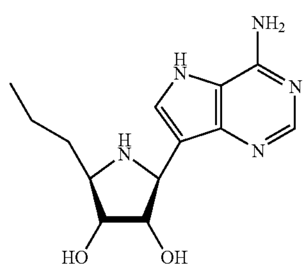 | 121 ± 5 pM | 38 ± 5 pM |
| 5'-methylthio-8-aza-ImmA | 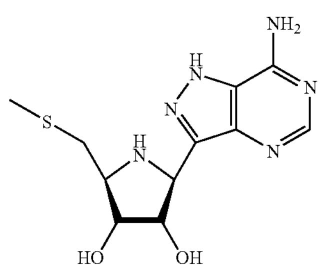 | 55 ± 3 pM | 26 ± 0.3 pM |

TABLE 1-continued

Inhibition Constants for MTAN Inhibitors

| Inhibitor Name | Structure | Ki | Ki* |
|---|---|---|---|
| 5'-Hydroxyethylthio-ImmA | 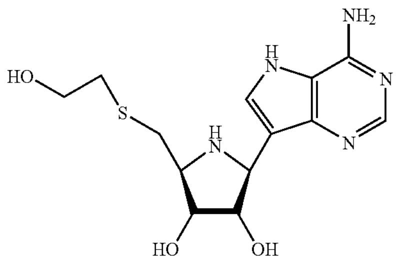 | 407 ± 16 pM | N. D. |
| 5'-Fluoroethylthio-ImmA | 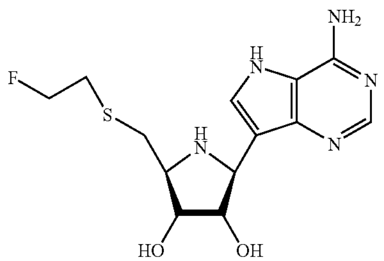 | 103 ± 11 pM | 30 ± 3 pM |
| 5'-Phenylthio-ImmA | 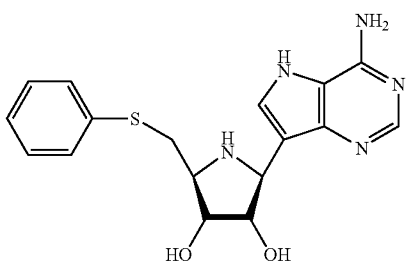 | 46.0 ± 3.0 pM | 32 ± 2.0 pM |
| 5'-deoxy-ImmA | 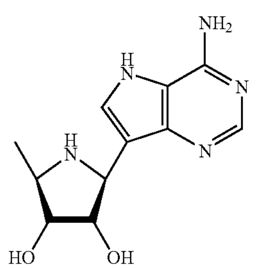 | 13 ± 1 nM | N. D. |
| 5'-Methoxy-ImmA | 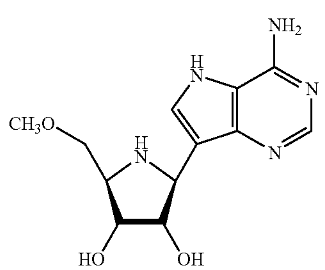 | 10 ± 1.0 nM | N. D. |

TABLE 1-continued

Inhibition Constants for MTAN Inhibitors

| Inhibitor Name | Structure | Ki | Ki* |
|---|---|---|---|
| 5'-(p-Fluoro-phenyl-thio)-ImmA | 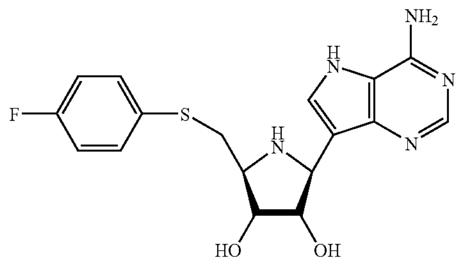 | 82.0 ± 7.0 pM | 20 ± 4.0 pM |
| 5'-(p-Chloro-Phenyl-thio)-ImmA | 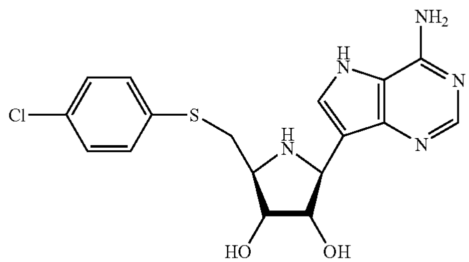 | 6.0 ± 0.3 pM | No late onset. Ki* is same as Ki i.e. 6 pM |
| 5'-(m-Chloro-Phenyl-thio)-ImmA | 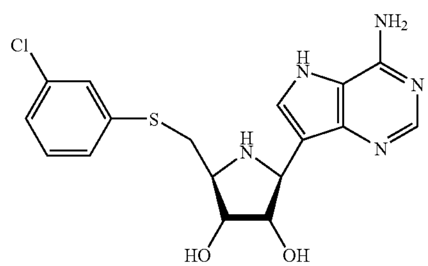 | 44.0 ± 4 pM | 20 ± 2.0 pM |
| 5'-Benzylthio-ImmA | 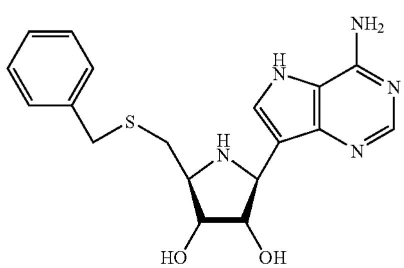 | 38.0 ± 3.0 pM | 12.0 ± 1.0 pM |
| 5'-(m-tolylthio)-ImmA | 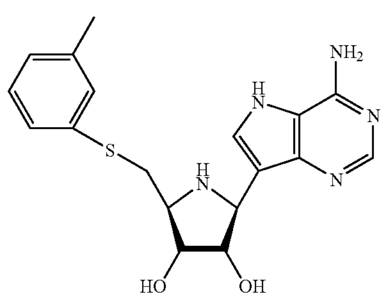 | 15.0 ± 0.6 pM | 9.0 ± 1.0 pM |

TABLE 1-continued

Inhibition Constants for MTAN Inhibitors

| Inhibitor Name | Structure | Ki | Ki* |
|---|---|---|---|
| 5'-(p-tolylthio)-ImmA | 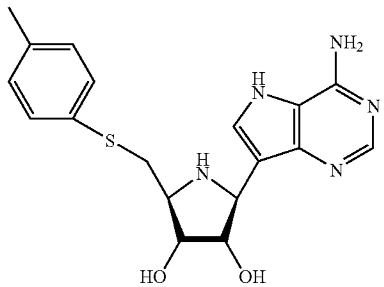 | 18.0 ± 1.0 pM | 8.0 ± 1.0 pM |
| 5'-Napthylthio-ImmA | 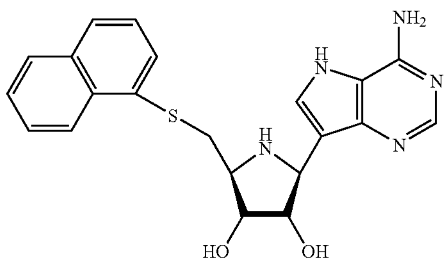 | 750 ± 33 pM | ND |

TABLE 2

Inhibition Constants for MTAP Inhibitors

| Inhibitor Name | Structure | Ki | Ki* |
|---|---|---|---|
| 5'-Phenylthio-ImmA | 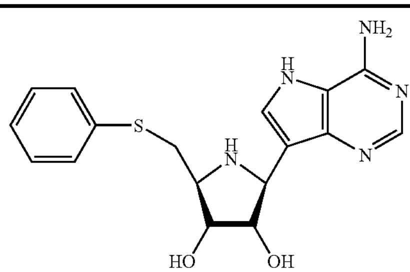 | 890.0 ± 120 pM | 82 ± 9 pM |
| 5'-Methylthio-ImmA | 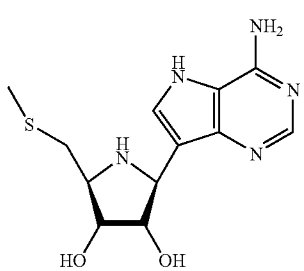 | 5.0 ± 0.5 nM | 90 ± 18 pM |
| 5'-Ethylthio-ImmA | 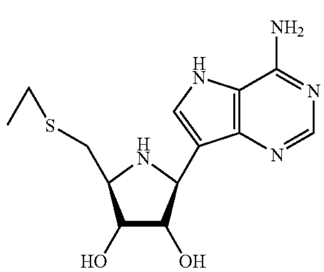 | 18.0 ± 2.0 nM | 260 ± 15 pM |

TABLE 2-continued

Inhibition Constants for MTAP Inhibitors

| Inhibitor Name | Structure | Ki | Ki* |
|---|---|---|---|
| 5'-Methylthio-8-aza-ImmA | 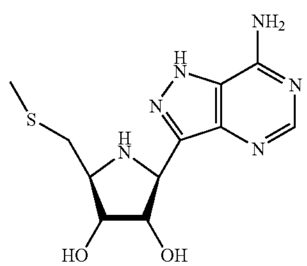 | 7.0 ± 1.0 nM | 760 ± 140 pM |
| 5'-(Hydroxyethylthio)-ImmA | 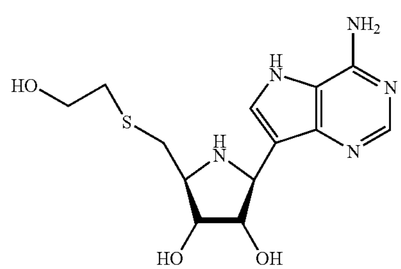 | 22.0 ± 2.0 nM | Ki* not determinable |
| 5'-(Fluoroethylthio)-ImmA | 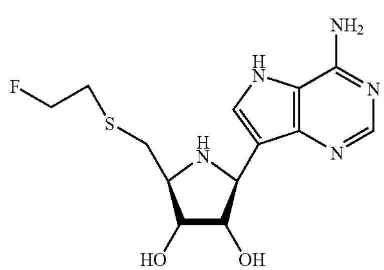 | 7.0 ± 0.5 nM | 1.5 ± 0.17 nM |
| 5'-deoxy-ImmA | 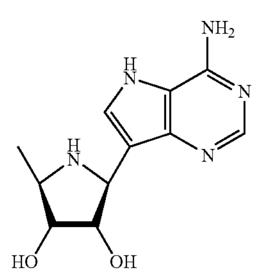 | 220 ± 14 nM | Ki* not determinable |
| 5'-Methoxy-ImmA | 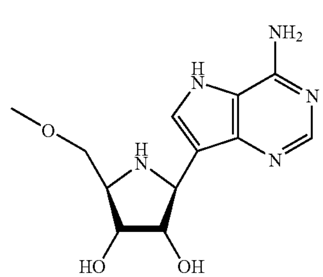 | 70 ± 5 nM | Ki* not determinable |

TABLE 2-continued

Inhibition Constants for MTAP Inhibitors

| Inhibitor Name | Structure | Ki | Ki* |
|---|---|---|---|
| 5'-(p-Fluoro-phenyl-thio)-ImmA | 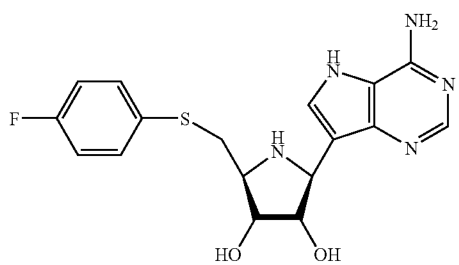 | 3.0 ± 0.2 nM | ND |
| 5'-(p-Chloro-phenyl-thio)-ImmA | 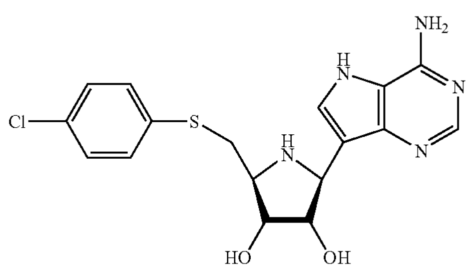 | 334 ± 36 pM | 90 ± 20 pM |
| 5'-(m-Chloro-phenyl-thio)-ImmA | 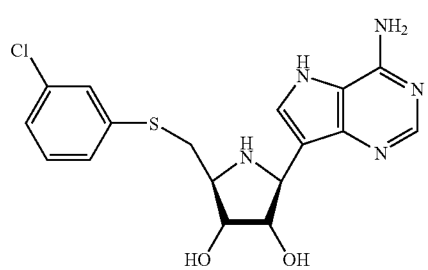 | 4.0 ± 0.4 nM | ND |
| 5'-Benzylthio-ImmA | 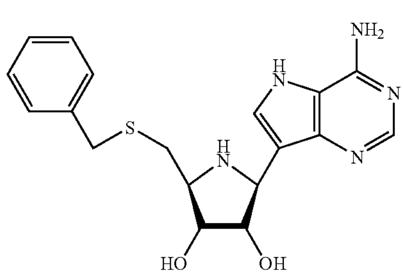 | 12 ± 1 nM | ND |

TABLE 2-continued

Inhibition Constants for MTAP Inhibitors

| Inhibitor Name | Structure | Ki | Ki* |
|---|---|---|---|
| 5'-(m-Tolylthio)-ImmA | 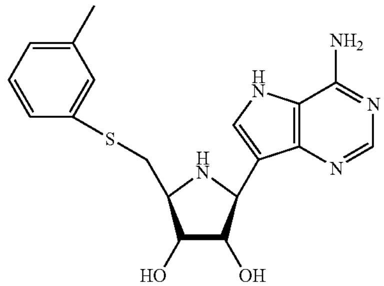 | 602 ± 32 pM | 146 ± 48 pM |
| 5'-(p-Tolylthio)-ImmA | 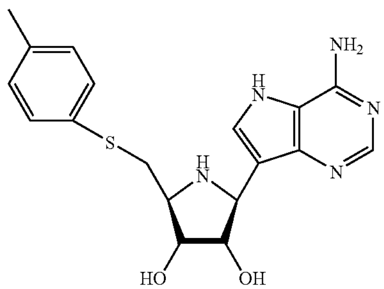 | 1.6 ± 0.2 nM | 252 ± 23 pM |
| 5'-Napthylthio-ImmA | 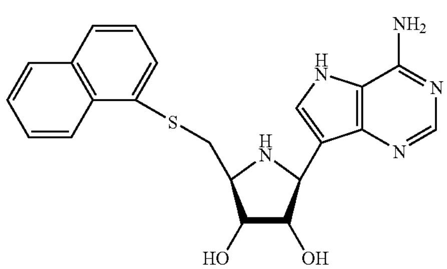 | 52 ± 5 nM | ND |

FIG. 1 shows the inhibition of MTAP by 5'-methylthio-ImmA at varying concentrations. (MTA at 150 μM; $K_m$=2.5 μM, $K_i$=107 pM).

Demonstration of Radiation Sensitizing Effect of 5'-methylthio-ImmA

Figure 2:
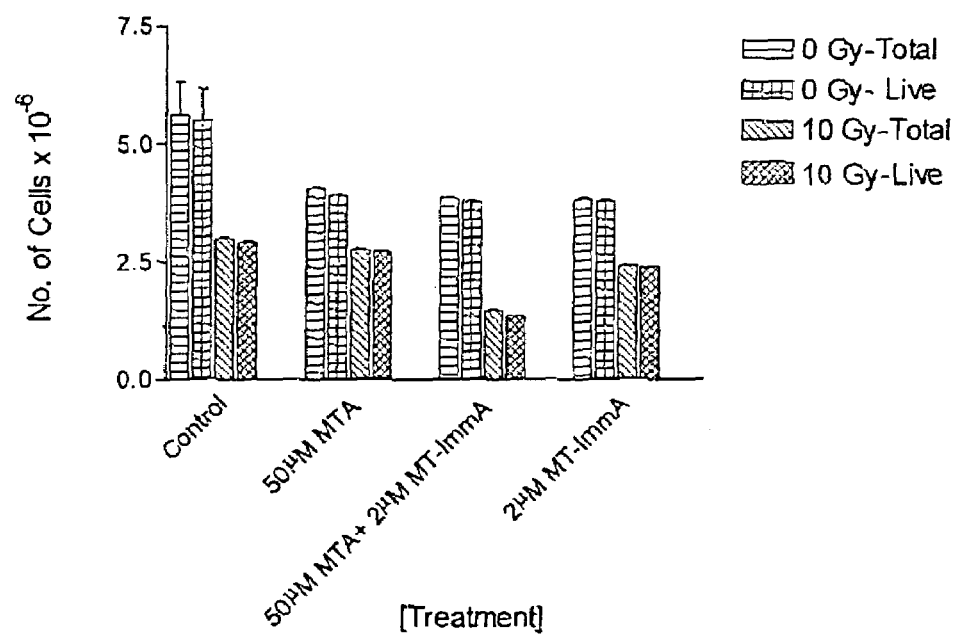
FIG. 2 shows the effect of methylthioadenosine (MTA) alone, 5'-methylthio-ImmA alone and a combination of MTA and 5'-methylthio-ImmA on the irradiation of Lewis Lung carcinoma cells.

FIG. 2 shows the effect of methylthioadenosine (MTA) alone, 5'-methylthio-ImmA alone and a combination of MTA and 5'-methylthio-ImmA on the irradiation of Lewis Lung carcinoma cells. These data show that the combination of MTA and 5'-methylthio-ImmA acts as a radiation sensitizer, lowering cell numbers after irradiation.

Further Aspects

The active compounds can be administered in combination with one or more conventional pharmaceutical carriers or excipients, and may be administered by a variety of routes, including oral administration, injection, or topical administration. The amount of compound to be administered will vary widely according to the nature of the patient and the nature and extent of the disorder to be treated. Typically the dosage for an adult human will be in the range less than 1 to 1000 milligrams, preferably 0.1 to 100 milligrams.

For oral administration the compounds can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid and the lubricant may be magnesium stearate. Other components such as colourings or flavourings may be added.

Liquid forms include carriers such as water and ethanol, with or without other agents such as a pharmaceutically acceptable surfactant or suspending agent.

The compounds may also be administered by injection in a physiologically acceptable diluent such as water or saline. The diluent may comprise one or more other ingredients such as ethanol, propylene glycol, an oil or a pharmaceutically acceptable surfactant.

The compounds may be present as ingredients in creams, for topical administration to skin or mucous membranes. Preferably the creams include a pharmaceutically acceptable solvent to assist passage through the skin or mucous membranes. Suitable creams are well known to those skilled in the art.

The compounds may further be administered by means of sustained release systems. For example, they may be incorporated into a slowly dissolving tablet or capsule.

The invention will be described in more detail with reference to the following non-limiting examples.

EXAMPLES

Example 1

Preparation of (1S)-1-(9-deazaadenin-9-yl)-1,4-dideoxy-1,4-imino-5-methylthio-D-ribitol (5'-methylthio-Immucillin-A, Scheme 1)

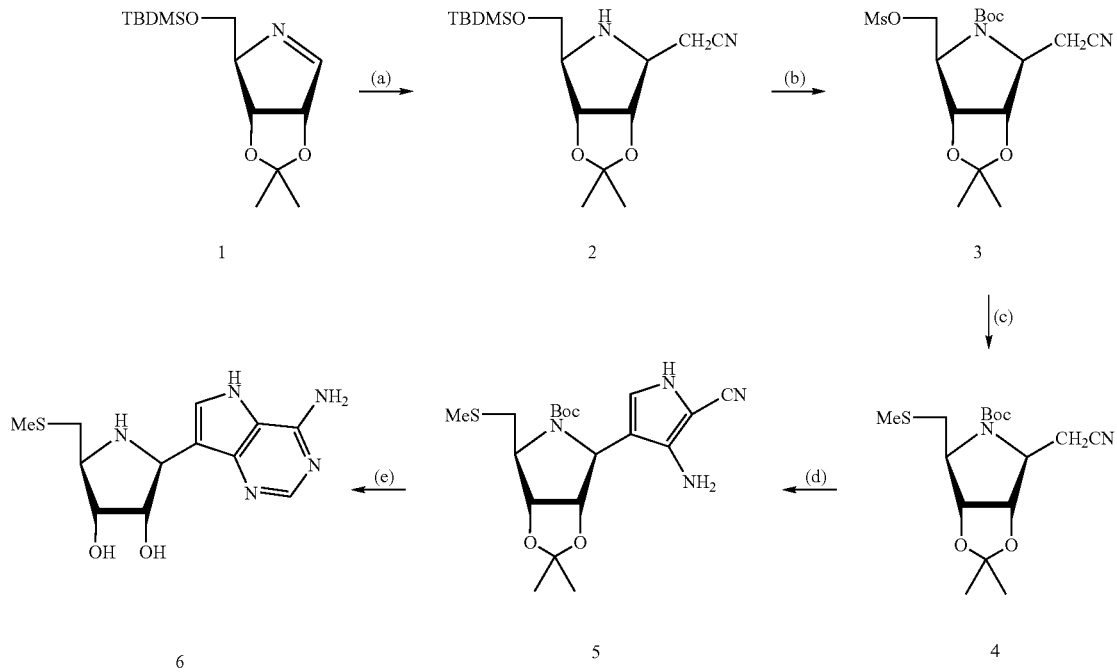

Scheme 1

Example 1.1

N-tert-Butoxycarbonyl-3,6-imino-4,5-O-isopropylidene-7-O-methanesulfonyl-2,3,6-trideoxy-D-allo-heptononitrile (3)

TBAF (5 mL, 1M in THF, 5.0 mmol) was added dropwise to a stirred solution of 7-O-tert-butyldimethylsilyl-3,6-imino-4,5-O-isopropylidene-2,3,6-trideoxy-D-allo-heptononitrile (2) (1.40 g, 4.3 mmol) in THF (20 mL) at room temperature. After 1 h the reaction was complete by TLC. The solution was diluted with water (200 mL) and extracted with chloroform (3×50 mL). The organic layers were combined, dried (MgSO$_4$) and concentrated in vacuo. The crude residue (0.92 g, 4.3 mmol) was dissolved in methanol (20 mL) and di-tert-butyl dicarbonate (1.00 g, 4.6 mmol) was added portionwise at room temperature and the resulting solution left to stir for 1 h. The reaction was concentrated in vacuo and chromatography of the residue presumably afforded N-tert-butoxycarbonyl-3,6-imino-4,5-O-isopropylidene-7-O-methanesulfonyl-2,3,6-trideoxy-D-allo-heptononitrile (1.1 g) as an oil. A solution of the oil in anhydrous dichloromethane (20 mL) and N-ethyidiisopropylamine (2 mL, 11.4 mmol) was treated with methanesulfonyl chloride (0.5 mL, 6.5 mmol). After 0.5 h the solution was diluted with chloroform (100 mL), washed with 10% HCl (50 mL), water (50 mL) and brine (50 mL). The organic phase was dried (MgSO$_4$) and concentrated in vacuo. Chromatography afforded N-tert-butoxycarbonyl-3,6-imino-4,5-O-isopropylidene-7-O-methanesulfonyl-2,3,6-trideoxy-D-allo-heptononitrile (3) (800 mg, 48% overall yield) as a syrup. $^1$H NMR (CDCl$_3$) δ 4.75 (dd, J=5.7, 1.4 Hz, 1H), 4.61 (brs, 1H), 4.38 (brd, J=5.7 Hz, 2H), 4.19 (m, 2H), 3.07 (s, 3H), 2.81 (m, 2H), 1.50 (s, 12H), 1.35 (s, 3H); $^{13}$C NMR δ 154.0, 117.5, 113.3, 83.3, 82.4, 81.3, 68.6, 64.2, 61.5, 60.7, 37.7, 28.6, 27.6, 25.6, 21.8. HRMS (MH$^+$) calc. for C$_{16}$H$_{27}$N$_2$O$_7$S: 391.1539. Found: 391.1539.

Example 1.2

(1S)-N-tert-Butoxycarbonyl-1-C-cyanomethyl-1,4-dideoxy-1,4-imino-2,3-O-isopropylidene-5-methylthio-D-ribitol (4)

Sodium thiomethoxide (0.75 g, 10.7 mmol) was added to a solution of N-tert-butoxycarbonyl-3,6-imino-4,5-O-isopropylidene-7-O-methanesulfonyl-2,3,6-trideoxy-D-allo-heptononitrile (3) (0.85 g, 2.2 mmol) in DMF (10 mL) at room temperature. After stirring overnight the reaction was diluted with toluene (100 mL), washed with water (50 mL), brine (50 mL), dried (MgSO$_4$) and concentrated in vacuo. Chromatography afforded (1S)-1-N-tert-butoxycarbonyl-C-cyanomethyl-1,4-dideoxy-1,4-imino-2,3-O-isopropylidene-5-methylthio-D-ribitol (4) (0.66 g, 3.06 mmol, 88%) as a colourless foam. $^1$H NMR δ 4.68 (m, 2H), 4.13 (m, 2H), 2.79 (m, 3H), 2.59 (dd, J=13.5, 10.6 Hz, 1H), 2.18 (s, 3H), 1.50 (s, 3H), 1.48 (s, 9H), 1.35 (s, 3H); $^{13}$C NMR δ 154.2, 118.0, 113.1, 83.6, 82.6, 81.7, 63.9, 62.2, 37.0, 28.7, 27.6, 25.6, 21.9, 16.1. HRMS (MH$^+$) calc. for C$_{16}$H$_{27}$N$_2$O$_4$S: 343.1692. Found: 343.1700.

Example 1.3

(1S)-1-(3-Amino-2-cyanopyrrol-4-yl)-N-tert-butoxycarbonyl-1,4-dideoxy-1,4-imino-2,3-O-isopropylidene-5-methylthio-D-ribitol (5)

Brederecks reagent (1.5 mL) was added dropwise to a stirred solution of (1S)-N-tert-butoxycarbonyl-1-C-cyanomethyl-1,4-dideoxy-1,4-imino-2,3-O-isopropylidene-5-methylthio-D-ribitol (4) (0.66 g, 1.9 mmol) in DMF (20 mL) under an inert atmosphere at room temperature. The resulting solution was heated at 70° C. for 18 h and then cooled to room temperature, diluted with toluene (100 mL), washed water (50 mL), brine (50 mL), dried (MgSO$_4$) and concentrated in vacuo. The crude residue was dissolved in THF/acetic acid/water (1:1:1, v/v/v, 10 mL) at room temperature and stirred for 2 h. The reaction was then diluted with chloroform (100 mL) and the resulting mixture washed with water (2×25 mL), saturated aqueous sodium bicarbonate and then dried and concentrated in vacuo. The crude residue was redissolved in methanol (5 mL) and sodium acetate (500 mg, 6.1 mmol) and aminoacetonitrile hydrochloride (200 mg, 2.2 mmol) were added consecutively at room temperature and the resulting suspension left to stir for 16 h. The reaction was then concentrated in vacuo and partitioned between chloroform (100 mL) and water (50 mL). The organic layer was separated, washed with water (25 mL), brine (25 mL), dried and concentrated in vacuo. The crude residue was redissolved in dichloromethane (5 mL) and treated dropwise with DBU (2.25 mL, 20 mmol) and methylchloroformate (1.0 mL, 12.7 mmol) and the resulting solution heated under reflux for 1 h. The reaction was then cooled and diluted with methanol (20 mL) and left for a further 1 h. The resulting solution was diluted with chloroform (250 mL), washed with dilute aqueous HCl, aqueous sodium bicarbonate, dried and concentrated in vacuo. Chromatography of the resultant residue afforded (1S)-1-(3-amino-2-cyanopyrrol-4-yl)-N-tert-butoxycarbonyl-1,4-dideoxy-1,4-imino-2,3-O-isopropylidene-5-methylthio-D-ribitol (5) (380 mg, 69%) as an oil. $^1$H NMR δ 7.80 (s, 1H), 5.68 (s, 1H), 5.22 (s, 1H), 4.63 (d, J=5.6 Hz, 1H), 4.50 (d, J=5.6 Hz, 1H), 4.31 (brs, 1H), 2.51 (dd, J=13.6, 3.7 Hz, 1H), 2.14 (m, 1H), 1.87 (s, 3H), 1.45 (s, 3H), 1.35 (s, 9H), 1.23 (s, 3H); $^{13}$C NMR (C$_6$D$_6$) δ 155.2 (C), 128.3, 120.2 (CH), 115.2, 112.6, 112.0, 87.2 (C), 84.6, 84.2 (CH), 80.5, (C), 64.6, 59.4 (CH), 37.0 (CH$_2$), 28.3, 27.4, 25.5, 14.5 (CH$_3$). HRMS (MH$^+$) calc. for C$_{19}$H$_{28}$N$_4$O$_4$S: 408.1831. Found: 408.1842

Example 1.4

(1S)-1-(9-Deazaadenin-9-yl)-1,4-dideoxy-1,4-imino-5-methylthio-D-ribitol (6)

(1S)-1-(3-Amino-2-cyanopyrrol-4-yl)-N-tert-butoxycarbonyl-1,4-dideoxy-1,4-imino-2,3-O-isopropylidene-5-methylthio-D-ribitol (5) (90 mg, 0.22 mmol) was dissolved in ethanol (5 mL), formamidine acetate (45 mg, 0.43 mmol) was added and the resulting suspension heated at reflux for 16 h. The crude reaction mixture was preabsorbed onto silica and chromatography afforded an oil which was not characterised but redissolved in methanol (1.5 mL) and stirred with concentrated HCl (1.5 mL) for 2 h. The crude reaction was concentrated in vacuo to afford (1S)-1-(9-deazaadenin-9-yl)-1,4-dideoxy-1,4-imino-5-methylthio-D-ribitol (6) (65 mg, 90%) as a hydrochloride salt which decomposed between 223–225° C. without melting. $^1$H NMR (D$_2$O) δ 8.33 (s, 1H), 7.97 (s, 1H), 4.90 (d, J=8.4 Hz, 1H), 4.75 (m, 1H), 4.38 (t, J=4.2 Hz, 1H), 3.87 (quintet, J=4.8 Hz, 1H), 3.05 (dd, J=14.4, 5.7 Hz, 1H), 2.91 (dd, J=14.4, 9.3 Hz, 1H), 2.11 (s, 3H); $^{13}$C NMR (D$_2$O) δ 149.4 (C), 143.6 (CH), 139.1 (C), 133.0 (CH), 113.0, 105.6 (C), 73.2, 72.5 63.6, 56.3 (CH), 33.5 (CH$_2$), 14.6 (CH$_3$). HRMS (MH$^+$) calc. for C$_{12}$H$_{18}$N$_5$O$_2$S: 296.1181. Found: 296.1171. Anal. calc. for C$_{12}$H$_{18}$N$_5$O$_2$·HCl C, 39.14; H, 5.20; Cl, 19.25; N, 19.02; S, 8.71. Found C, 38.96; H, 5.28; Cl, 19.25; N, 18.82; S, 8.61.

Example 2

Preparation of (1S)-1-(9-deazaadenin-9-yl)-1,4-dideoxy-1,4-imino-5-O-methyl-D-ribitol hydrochloride (5'-O-methyl-Immucillin-A, Scheme 2)

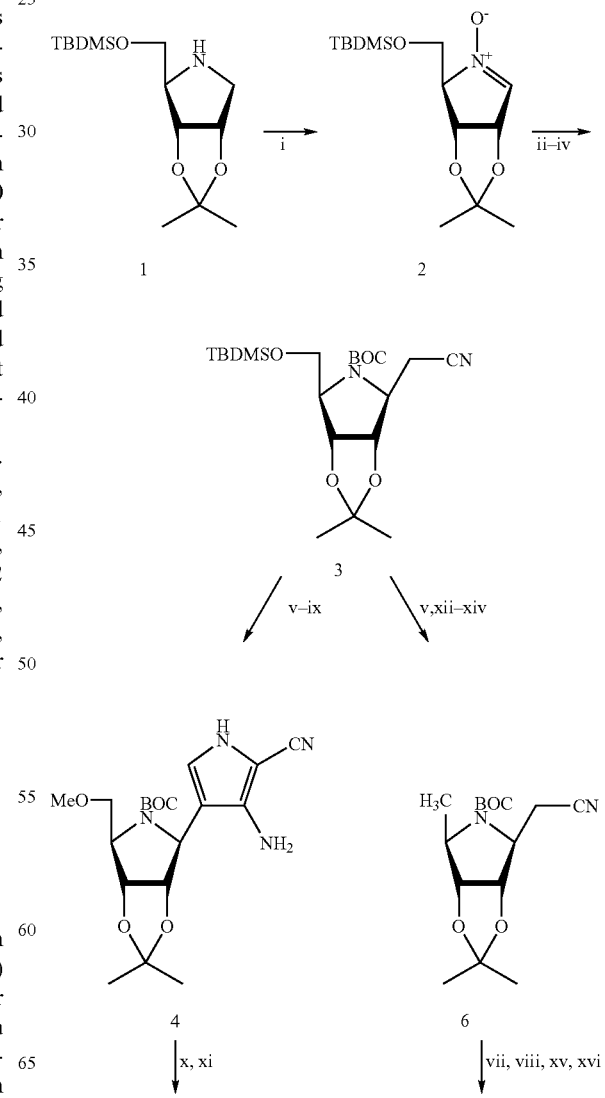

Scheme 2

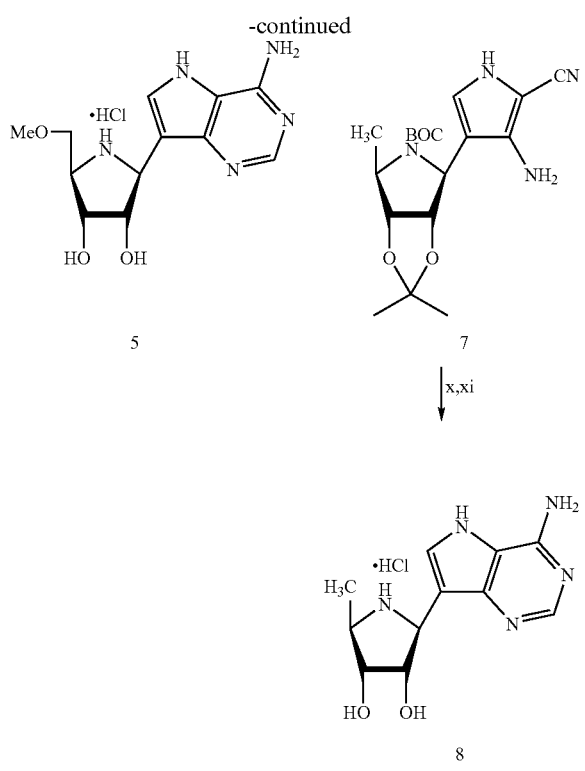

Example 2.1

5-O-tert-Butyldimethylsilyl-1,N-dehydro-1,4-dideoxy-1,4-imino-2,3-O-isopropylidene-D-ribitol N-oxide (2)

Selenium dioxide (0.6 g) was added to a solution of 5-O-tert-butyldimethylsilyl-1,4-dideoxy-1,4-imino-2,3-O-isopropylidene-D-ribitol (1) (Horenstein, B. A.; Zabinski, R. F.; Schramm, V. L. *Tetrahedron Lett.*, 1993, 34, 7213) (30 g) in acetone (50 mL) and the solution was cooled to 0° C. 30% Hydrogen peroxide (~40 mL) was added slowly keeping the solution at <4° C. until t.l.c. indicated that the reaction was complete, then chloroform (250 mL) was added and the mixture was washed with water (500 mL). The organic phase was dried and concentrated to dryness. Chromatography of the residue afforded 5-O-tert-Butyldimethylsilyl-1,N-dehydro-1,4-dideoxy-1,4-imino-2,3-O-isopropylidene-D-ribitol N-oxide (2) (18.3 g) as a solid with m.p. 121–124° C. Anal. calc. for $C_{14}H_{27}NO_4Si$: C, 55.78; H, 9.03; N, 4.65; found: C, 55.81; H, 8.88; N, 4.75. $^1H$ NMR (CDCl$_3$) δ 6.84 (s, 1H), 5.09 (m, 1H), 4.79 (d, 1H, J=6.2 Hz), 4.20 J=2.0, 11.0 Hz), 3.99 (d, 1H, J=0.7 Hz), 3.80 (dd, 1H, J=2.1, 11.0 Hz), 1.33 (s, 3H), 1.38 (s, 3H), 0.81 (s, 9H), 0.02, (s, 3H), 0.00, (s, 3H); $^{13}C$ NMR δ 133.48, 111.97, 81.11, 79.49, 77.48, 60.21, 27.72, 26.25, 26.10, 18.50.

Example 2.2

N-tert-Butoxycarbonyl-7-O-tert-butyldimethylsilyl-2,3,6-trideoxy-3,6-imino-4,5-O-isopropylidene-D-allo-heptononitrile (3)

Butyl lithium (32.5 mL, 2.3 M, 74.8 mmol) was added to THF (300 mL) and the solution was cooled to –70° C., then acetonitrile (4.2 mL, 80.2 mmol) was added slowly keeping the reaction temperature <–65° C. After 30 min. a solution of 5-O-tert-butyldimethylsilyl-1,N-dehydro-1,4-dideoxy-1,4-imino-2,3-O-isopropylidene-D-ribitol N-oxide (2) (15 g, 49.8 mmol) in THF (30 mL) was added. The resulting solution was stirred at –70° C. for 30 min. then quenched with water. Petroleum ether (500 mL) was added and the mixture was washed with water, and processed normally to give a syrup. A solution of this material in acetic acid (100 mL) was stirred while zinc dust (20 g) was added. Cooling was applied as necessary to keep the reaction temperature <30° C. After stirring for 6 h the mixture was filtered and the filtrate was concentrated to a syrup. A solution of this in chloroform (200 mL) was washed with aq. NaHCO$_3$, dried, and then di-tert-butyl dicarbonate (11.5 g) was added. After standing overnight the solution was concentrated to dryness and chromatography afforded N-tert-Butoxycarbonyl-7-O-tert-butyldimethylsilyl-2,3,6-trideoxy-3,6-imino-4,5-O-isopropylidene-D-allo-heptononitrile (3) (15.9 g) as a syrup with identical NMR spectra to that reported (Evans, G. B.; Furneaux, R. H.; Gainsford, G. J.; Schramm, V. L.; Tyler, P. C. *Tetrahedron* 2000, 56, 3053).

Example 2.3

(1S)-1-(3-Amino-2-cyanopyrrol-4-yl)-N-tert-butoxycarbonyl-1,4-dideoxy-1,4-imino-2,3-O-isopropylidene-5-O-methyl-D-ribitol (4)

Tetrabutylammonium fluoride (2.5 mL, 1M in THF) was added to a solution of N-tert-butoxycarbonyl-7-O-tert-butyldimethylsilyl-2,3,6-trideoxy-3,6-imino-4,5-O-isopropylidene-D-allo-heptononitrile (3) (0.5 g) in THF (2.5 mL). After 1 h chloroform (20 mL) was added and the solution was washed with water, dried and concentrated to dryness. A solution of the residue in THF (10 mL) and methyl iodide (0.25 mL) was stirred while sodium hydride (0.1 g, 60%) was added and the resulting mixture was stirred for 2 h. After quenching with ethanol, chloroform was added and the mixture was washed with water, dried and concentrated to dryness. A solution of the crude product in THF (5 mL) and ethyl formate (1.2 mL) was stirred with sodium hydride (0.25 g, 60%) for 2 h. Acetic acid (0.6 mL) was added followed by chloroform and the mixture was washed with water, dried and concentrated to dryness. A solution of the crude product in methanol (10 mL) containing sodium acetate (1.2 g) and aminoacetonitrile hydrochloride (0.7 g) was heated under reflux for 1 h. Chloroform was added and the solution was washed with water, dried and concentrated to dryness. A solution of the residue in methylene chloride (10 mL) containing DBU (0.54 mL) and methyl chloroformate (0.14 mL) was heated under reflux for 0.5 h. Methanol (5 mL) was added to the cooled solution and after 1 h the solution was processed normally to give, after chromatography, (1S)-1-(3-amino-2-cyanopyrrol-4-yl)-N-tert-butoxycarbonyl-1,4-dideoxy-1,4-imino-2,3-O-isopropylidene-5-O-methyl-D-ribitol (4) (0.091 g) as a syrup. $^1H$ NMR (CDCl$_3$) δ 8.70 (s, 1H), 6.42 (d, J=3.2 Hz, 1H), 4.79 (bs, 1H), 4.67 (m, 2H), 4.14–3.98 (m, 3H), 3.35 (m, 2H), 3.25 (s, 3H), 1.45 (s, 3H), 1.36 (s, 9H), 1.27 (s, 3H); $^{13}C$ NMR δ 154.2, 141.5 (C), 120.4 (CH), 114.2, 111.4, 111.0, 85.6 (C), 83.2, 81.3 (CH), 79.7 (C), 71.4 (CH$_2$), 63.1, 59.2 (CH), 57.9, 27.4, 26.5, 24.6 (CH$_3$).

Example 2.4

(1S)-1-(9-Deazaadenin-9-yl)-1,4-dideoxy-1,4-imino-5-O-methyl-D-ribitol hydrochloride (5)

A solution of (1S)-1-(3-amino-2-cyanopyrrol-4-yl)-N-tert-butoxycarbonyl-1,4-dideoxy-1,4-imino-2,3-O-isopropylidene-5-O-methyl-D-ribitol (4) (0.09 g) in ethanol (5 mL) containing formamidine acetate (0.048 g) was heated under reflux for 3 h and then concentrated to dryness. Chromatography of the residue gave the product which was dissolved in methanol (5 mL) and conc. HCl (5 mL), allowed to stand overnight, and then concentrated to dryness to give (1S)-1-(9-deazaadenin-9-yl)-1,4-dideoxy-1,4-imino-5-O-methyl-D-ribitol hydrochloride (5) as a solid (0.068 g). $^1$H NMR (D$_2$O) δ 8.44 (s, 1H), 8.05 (s, 1H), 5.01 (d, J=8.9 Hz, 1H), 4.81 (dd, J=8.9, 4.8 Hz, 1H), 4.48 (dd, J=4.8, 3.4 Hz, 1H), 4.03–3.98 (m, 1H), 3.85 (dd, J=11.2, 5.4 Hz, 1H), 3.79 (dd, J=11.2, 3.9 Hz, 1H), 3.43 (s, 3H); $^{13}$C NMR δ 149.8 (C), 143.9 (CH), 138.6 (C),132.9 (CH), 113.0, 105.5 (C), 73.8, 71.2 (CH), 68.9 (CH$_2$), 64.3 (CH), 59.1 (CH$_3$), 55.9 (CH).

Example 3

Preparation of (1S)-1-(9-deazaadenin-9-yl)-1,4,5-trideoxy-1,4-imino-D-ribitol hydrochloride (5'-deoxy-Immucillin-A, Scheme 2)

Example 3.1

N-tert-Butoxycarbonyl-2,3,6,7-tetradeoxy-3,6-imino-4,5-O-isopropylidene-D-allo-heptononitrile (6)

Tetrabutylammonium fluoride (4 mL, 1M in THF) was added to a solution of N-tert-Butoxycarbonyl-7-O-tert-butyldimethylsilyl-2,3,6-trideoxy-3,6-imino-4,5-O-isopropylidene-D-allo-heptononitrile (3) (0.75 g) in THF (4 mL). After 1 h chloroform (20 mL) was added and the solution was washed with water, dried and concentrated to dryness. A solution of the residue in dry methylene chloride (10 mL) was treated with diisopropylethylamine (0.92 mL) and then methanesulfonyl chloride (0.2 mL). After 0.5 h, the solution was washed with 2M aq. HCl, aq. NaHCO$_3$, dried and concentrated to dryness. A solution of the product in acetone (10 mL) containing sodium iodide (1.3 g) was heated under reflux for 24 h, and then concentrated to dryness. Chloroform was added and the mixture was washed with water, dried and concentrated to dryness. Tributyltin hydride (1.0 mL) was added to a solution of the crude product in benzene (10 mL) and the solution was heated under reflux. After 0.5 h more tributyltin hydride (0.5 mL) was added and refluxing was continued for a further 1 h. The solution was concentrated to dryness and the residue was redissolved in ether. This solution was stirred with 10% aq. KF for 1 h, then the organic layer was collected, dried and concentrated to dryness. Chromatography of the residue afforded N-tert-Butoxycarbonyl-2,3,6,7-tetradeoxy-3,6-imino-4,5-O-isopropylidene-D-allo-heptononitrile (6) (0.34 g) as a syrup. $^1$H NMR (CDCl$_3$) δ 4.66 (dd, J=5.6, 2.4 Hz, 1H), 4.44 (dd, J=5.6, 1.3 Hz, 1H), 4.10–4.05 (m, 2H), 2.90–2.72 (m, 2H), 1.48 (s, 12H), 1.33 (s, 3H), 1.32 (d, J=7.0 Hz, 3H); $^{13}$C NMR δ 154.3, 117.9, 112.9 (C), 85.4, 82.9 (CH), 81.1 (C), 61.8, 60.2 (CH), 28.7, 27.7, 25.7 (CH$_3$), 22.4 (CH$_2$), 20.3 (CH$_3$).

Example 3.2

(1S)-1-(9-Deazaadenin-9-yl)-1,4,5-trideoxy-1,4-imino-D-ribitol hydrochloride (8)

A solution of N-tert-butoxycarbonyl-2,3,6,7-tetradeoxy-3,6-imino-4,5-O-isopropylidene-D-allo-heptononitrile (6) (0.33 g) in THF (10 mL) containing ethyl formate (0.9 mL) was stirred with sodium hydride (0.18 g, 60%) for 3 h. Acetic acid (0.5 mL) was added followed by chloroform and the mixture was washed with water, dried and concentrated to dryness. A solution of the crude product in methanol (15 mL) containing sodium acetate (0.91 g) and aminoacetonitrile hydrochloride (0.52 g) was stirred at room temperature for 3 days. Chloroform was added and the solution was washed with water, dried and concentrated to dryness. A solution of the residue in methylene chloride (20 mL) containing DBU (0.85 mL) and methyl chloroformate (0.15 mL) was heated under reflux for 1 h. The cooled solution was washed with 2M aq. HCl, aq. NaHCO$_3$ dried and concentrated to dryness. Triethylamine (1 mL) was added to a solution of this material in methanol (10 mL) and after 3 h the solution was concentrated to dryness. Chromatography afforded (1S)-1-(3-amino-2-cyanopyrrol-4-yl)-N-tert-butoxycarbonyl-1,4,5-trideoxy-1,4-imino-2,3-O-isopropylidene-D-ribitol (7) (0.36 g). A solution of this material in ethanol (10 mL) containing formamidine acetate (0.207 g) was heated under reflux for 3 h and then concentrated to dryness. After chromatography of the residue the product was dissolved in methanol (5 mL) and conc. aq. HCl (5 mL), the solution was allowed to stand at room temperature for 3 h and then concentrated to dryness. Trituration of the residue with ethanol afforded (1S)-1-(9-deazaadenin-9-yl)-1,4,5-trideoxy-1,4-imino-D-ribitol hydrochloride (8) (0.218 g) as a white solid. $^1$H NMR (D$_2$O) δ 8.41 (s, 1H), 8.04 (s, 1H), 4.96 (d, J=8.5 Hz, 1H), 4.88 (dd, J=8.5, 4.8 Hz, 1H), 4.31 (t, J=4.5 Hz, 1H), 3.87 (dq, J=7.1, 4.2 Hz, 1H), 1.54 (d, J=7.1 Hz, 3H); $^{13}$C NMR δ 149.5 (C), 143.7 (CH), 139.2 (C), 132.8 (CH), 113.2, 106.2 (C), 74.5, 73.2, 60.8, 56.2 (CH), 16.0 (CH$_3$).

Example 4

Preparation of (1S)-1-(7-Amino-1H-pyrazolo[4,3-d]pyrimidin-3-yl)-1,4-dideoxy-1,4-imino-5-methylthio-D-ribitol.2HCl (8-aza-5'-methylthio-Immucillin-A, Scheme 3)

Scheme 3

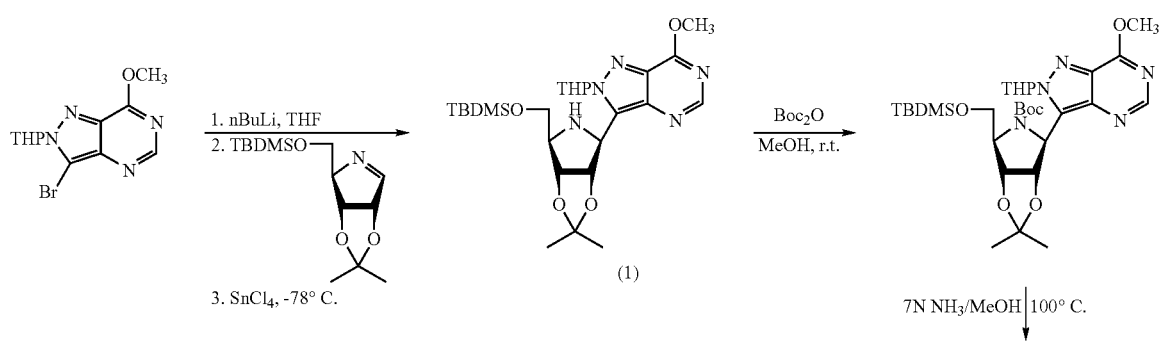

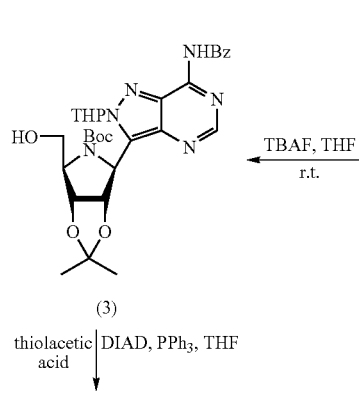
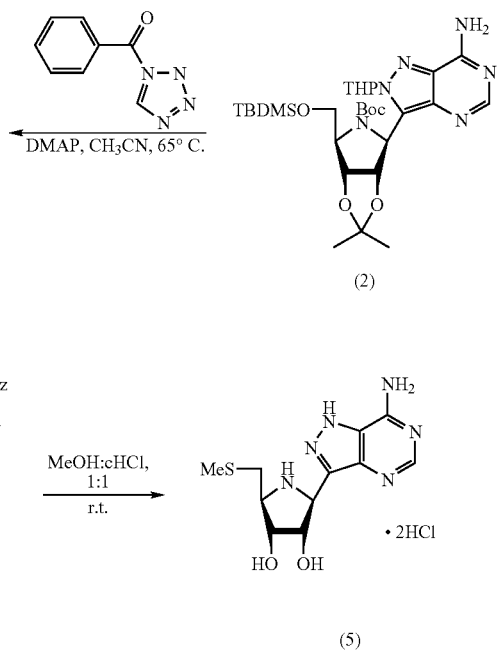
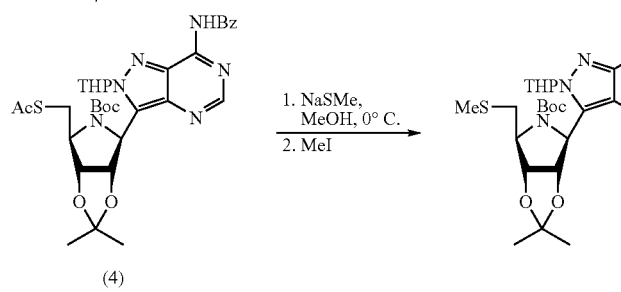

Example 4.1

(1S)-5-O-tert-Butyldimethylsilyl-1,4-dideoxy-1,4-imino-2,3-O-isopropylidene-1-(7-methoxy-2-tetrahydropyran-2-yl-1H-pyrazolo[4,3-d]pyrimidin-3-yl)-D-ribitol (1)

n-BuLi (1.6M, 8.2 mL, 13.1 mmol) was added dropwise to a stirred solution of 3-bromo-7-methoxy-2-(tetrahydropyran-2-yl)-pyrazolo[4,3-d]pyrimidine (4.3 g, 13.7 mmol) and anhydrous THF (30 mL) at −78° C. until no starting material remains. A THF (10 mL) of imine (3.5 g, 12.3 mmol), dissolved in THF (30 mL), was added dropwise via cannula followed by SnCl$_4$ (0.51 ml, 4.4 mmol) at such a rate that the reaction temperature was maintained below −70° C. The reaction mixture was allowed to warm to r.t. and then quenched by addition of 15% NaOH (30 ml). Diethyl ether (200 ml) was added and the organic phase separated, dried (MgSO$_4$) and concentrated in vacuo. Chromatography afforded (1S)-5-O-tert-butyldimethylsilyl-1,4-dideoxy-1,4-imino-2,3-O-isopropylidene-1-(7-methoxy-2-tetrahydropyran-2-yl-1H-pyrazolo[4,3-d]pyrimidin-3-yl)-D-ribitol (1) (2.8 g, 44%) as a clear oil. This exists as a diastereomeric mixture because of the THP-group. $^1$H-NMR (CDCl$_3$): δ 8.37 (1H, s), 5.96, 5.86 (1H, m), 5.31, 4.98 (1H, m), 4.75 (2H, m), 4.15 (3H, s), 4.02–3.70 (4H, m), 3.33, 3.26 (1H, m), 2.60 (1H, m), 2.08 (2H, m) 1.70 (1H, m), 1.59, 1.56 (3H, s), 1.34, 1.32 (3H, s), 0.88, 0.85 (9H, s), 0.05, 0.03, 0.00 (6H, s). $^{13}$C-NMR (CDCl$_3$) δ 162.3, 151.4, 139.6, (135.5, 135.3), 131.7, (114.9, 114.4), (87.6, 87.1), (86.4, 85.9), (83.1, 82.8), (68.3, 68.0), (66.9, 66.4), (63.0, 62.3), (61.7, 61.5), 54.3, (30.0, 29.7), (28.0, 28.0), 26.2, (25.9, 25.8), 25.2, (22.8, 22.6), 18.6, −4.9.

Example 4.2

(1S)-1-(7-Amino-2-tetrahydropyran-2-yl-1H-pyrazolo[4,3-d]pyrimidin-3-yl)-N-(tert-butoxycarbonyl)-5-O-tert-butyldimethylsilyl-1,4-dideoxy-1,4-imino-2,3-O-isopropylidene-D-ribitol (2)

Di-tert-butyl dicarbonate (1.4 g, 6.5 mmol) was added portionwise to a stirred solution of (1S)-5-O-tert-butyldimethylsilyl-1,4-dideoxy-1,4-imino-2,3-O-isopropylidene-1-(7-methoxy-2-tetrahydropyran-2-yl-1H-pyrazolo[4,3-d]pyrimidin-3-yl)-D-ribitol (1) (2.8 g, 5.4 mmol) in methanol (40 mL) at room temperature. After 30 min the reaction was complete and purification by flash chromatography provided two separate diastereomers (2.2 g, 66%) as yellow oils. The faster running of the two diasteromers (900 mg, 1.45 mmol) was redissolved in 7N NH$_3$ in methanol and the resulting solution heated in a sealed tube at 100° C. overnight. The reaction was concentrated in vacuo and purification of the resulting residue by chromatography afforded (1S)-1-(7-Amino-2-tetrahydropyran-2-yl-1H-pyrazolo[4,3-d]pyrimidin-3-yl)-N-(tert-butoxycarbonyl)-5-O-tert-butyldimethylsilyl-1,4-dideoxy-1,4-imino-2,3-O-isopropylidene-D-ribitol (2) (0.52 g, 59%) as an oil. $^{13}$C-NMR (CDCl$_3$) δ 156.5, 155.5, 152.9, 136.4, 133.8, 131.7, 112.0, 85.9, 83.9, 80.8, 68.9, 62.7, 59.4, 31.5, 28.7, 27.7, 26.2, 25.8, 25.2, 23.2, 18.6, −4.9.

Example 4.3

(1S)-1-{7-N-Benzoyl-(7-amino-2-tetrahydropyran-2-yl-1H-pyrazolo[4,3-d]pyrimidin-3-yl)}-N-(tert-butoxycarbonyl)-1,4-dideoxy-1,4-imino-2,3-O-isopropylidene-D-ribitol (3)

(1S)-1-(7-Amino-2-tetrahydropyran-2-yl-1H-pyrazolo[4,3-d]pyrimidin-3-yl)-N-(tert-butoxycarbonyl)-5-O-tert-butyldimethylsilyl-1,4-dideoxy-1,4-imino-2,3-O-isopropylidene-D-ribitol (2) (200 mg, 0.33 mmol) was dissolved in acetonitrile and then benzoyl tetrazole (130 mg, 0.74 mmol) and DMAP (45 mg, 0.36 mmol) were added consecutively. The resulting solution was stirred at reflux for 0.5 h. and then cooled to r.t. The reaction was diluted with ethyl acetate and the organic layer washed with 10% HCl, saturated NaHCO$_3$ and brine, the organic layer was then dried (MgSO$_4$) filtered and concentrated in vacuo. The crude residue was redissolved in THF (5 mL) and treated with acetic acid (60 μL) and n-tetrabutylammonium fluoride (700 μL, 1M in THF) and allowed to stir for 48 h at r.t. The reaction was preabsorbed onto flash silica gel (5 g) and purified by chromatography to afford (1S)-1-{7-N-benzoyl-(7-amino-2-tetrahydropyran-2-yl-1H-pyrazolo[4,3-d]pyrimidin-3-yl)}-N-(tert-butoxycarbonyl)-1,4-dideoxy-1,4-imino-2,3-O-isopropylidene-D-ribitol (3) (190 mg, 97%) as an oil. $^{13}$C-NMR (CDCl$_3$) δ 154.1, 152.1, 138.5, 137.5, 134.9, 133.2, 132.1, 129.0, 128.8, 112.6, 88.4, 87.1, 85.6, 84.9, 83.6, 83.0, 80.8, 68.9, 68.1, 66.0, 63.0, 62.5, 60.7, 30.1, 28.6, 28.4, 26.0, 25.1, 22.9, 21.3.

Example 4.4

(1S)-5-acetylthio-1-{7-N-Benzoyl-(7-amino-2-tetrahydropyran-2-yl-1H-pyrazolo[4,3-d]pyrimidin-3-yl)}-N-(tert-butoxycarbonyl)-1,4-dideoxy-1,4-imino-2,3-O-isopropylidene-D-ribitol (4)

DIAD (0.13 mL, 0.65 mmol, 95%) was added dropwise to a THF (5 mL) solution of triphenylphosphine (0.17 g, 0.65 mmol) at 0° C. and left to stir. After 0.5 h a THF (5 mL) solution of (1S)-{N-benzoyl-(7-amino-2-tetrahydropyran-2-yl-1H-pyrazolo[4,3-d]pyrimidin-3-yl)}-N-(tert-butoxycarbonyl)-1,4-dideoxy-1,4-imino-2,3-O-isopropylidene-1-D-ribitol (3) (190 mg, 0.32 mmol) and thiolacetic acid (50 μL) was added dropwise maintaining the reaction at 0° C. and then the resulting solution was allowed to warm to r.t. After 1 h at r.t., the reaction was concentrated in vacuo and the resulting residue purified by chromatography to afford (1S)-5-acetylthio-1-{7-N-Benzoyl-(7-amino-2-tetrahydropyran-2-yl-1H-pyrazolo[4,3-d]pyrimidin-3-yl)}-N-(tert-butoxycarbonyl)-1,4-dideoxy-1,4-imino-2,3-O-isopropylidene-D-ribitol (4) (130 mg, 62%). $^{13}$C-NMR (CDCl$_3$) δ 194.8, 155.0, 152.0, 135.3, 133.0, 128.9, 112.7, 86.6, 84.9, 84.1, 81.4, 68.7, 66.3, 59.6, 30.8, 28.7, 27.7, 25.7, 25.1, 23.0, 22.3.

Example 4.5

(1S)-1-(7-Amino-1H-pyrazolo[4,3-d]pyrimidin-3-yl)-1,4-dideoxy-1,4-imino-5-methylthio-D-ribitol.2HCl (5)

A methanolic solution of sodium thiomethoxide (2 mL, 0.1 M) was added dropwise to a solution of (1S)-5-acetylthio-1-{N-benzoyl-(7-amino-2-tetrahydropyran-2-yl-1H-pyrazolo[4,3-d]pyrimidin-3-yl)}-N-(tert-butoxycarbonyl)1,4-dideoxy-1,4-imino-2,3-O-isopropylidene-D-ribitol (4) (80 mg, 0.12 mol) in anhydrous methanol and cooled to 0° C. The reaction was allowed to warm to r.t. and then left for 0.5 h after which time the reaction was quenched with methyl iodide (0.2 mL, xs) and the resulting reaction left to stir overnight. The reaction mixture was partitioned between chloroform and water, the organic layer separated and dried (MgSO$_4$) and the residue purified by chromatography. The resulting residue was dissolved in 1:1 cHCl:MeOH and left to stand overnight. Concentration in vacuo followed by trituration with methanol and diethyl ether yielded (1S)-1-(7-amino-1H-pyrazolo[4,3-d]pyrimidin-3-yl)-1,4-dideoxy-1,4-imino-5-methylthio-D-ribitol.2HCl (5).2HCl. $^1$H-NMR (D$_2$O) δ 8.44 (1H, s), 5.22 (1H, d, J 8.8 Hz), 4.80 (1H, t, J 4.9 Hz), 4.52 (1H, t, J 5.7 Hz), 3.99 (1H, dt, J 9.6, 5.7 Hz), 3.09 (2H, m), 2.19 (3H, s). $^{13}$C-NMR (D$_2$O) δ 152.11 (CH), 151.75, 138.8, 138.5, 123.3 (C), 74.3, 74.0, 62.3, 58.6 (CH), 35.0 (CH$_2$), 14.9 (CH$_3$).

Example 5

Preparation of (1S)-1-(9-deazaadenin-9-yl)-1,4-dideoxy-1,4-imino-5-(substituted)thio-D-ribitols (Scheme 4)

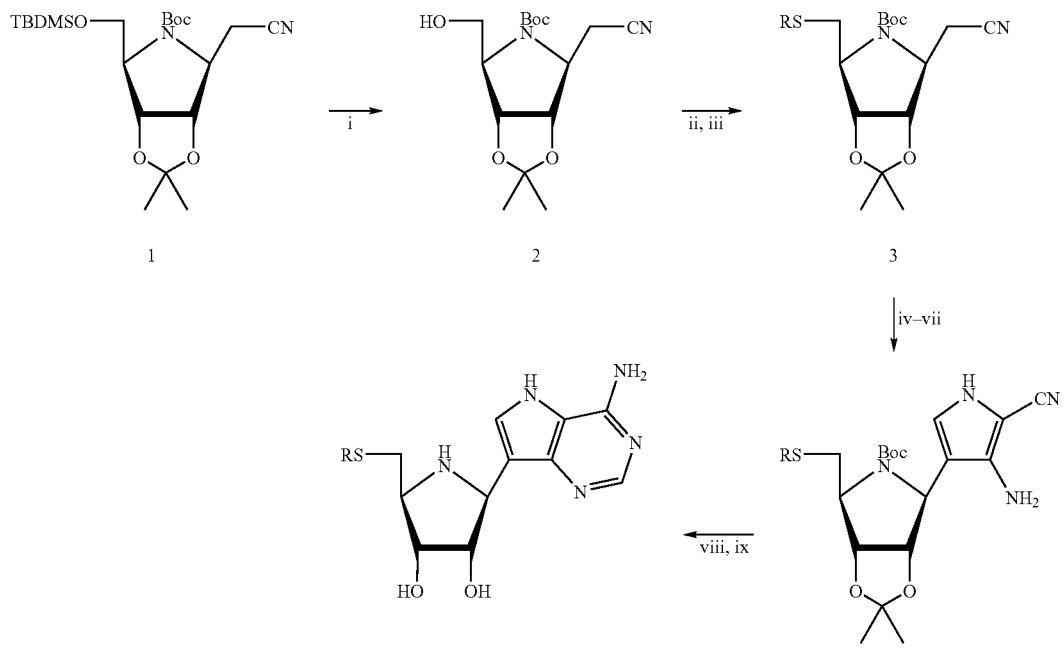

Example 5.1

N-Tert-butoxycarbonyl-3,6-imino-4,5-O-isopropylidene-2,3,6-trideoxy-D-allo-heptononitrile (2)

Tetrabutylammonium fluoride (75 mL, 1M in THF) was added to a solution of the product 1 (Scheme 4.3, prepared as described in Example 2.2) (19.1 g, 44.8 mmol) in THF (50 mL) and the solution was allowed to stand for 1 h. Chloroform (350 mL) was added and the solution was washed twice with water, dried and concentrated to dryness. Chromatography of the residue afforded N-tert-butoxycarbonyl-3,6-imino-4,5-O-isopropylidene-2,3,6-trideoxy-D-allo-heptononitrile (2) as a syrup (13.8 g, 98%). $^1$H NMR (CDCl$_3$) δ 4.6–4.05 (m, 4H), 3.61 (br s, 1H), 3.40 (br s, 1H), 2.7–2.2 (m, 3H), 1.35, (s, 12H), 1.14 (s, 3H).

Example 5.2

N-Tert-butoxycarbonyl-5-ethylthio-3,6-imino-4,5-O-isopropylidene-2,3,6-trideoxy-D-allo-heptononitrile (3, R=Et)

A solution of the product from example 5.1 (0.51 g) in dichloromethane (8 mL) was treated with diisopropylethylamine (0.56 mL) and methanesulfonyl chloride (0.185 mL). After 1 h, the solution was washed with dil HCl, aq NaHCO$_3$, dried and concentrated to dryness. A solution of the residue in DMF (2 mL) was added to a solution resulting from the addition of ethanethiol (0.24 mL) to a mixture of sodium hydride (0.13 g, 60% dispersion) in DMF (5 mL). The resulting mixture was stirred for 1 h, then toluene was added and the mixture was washed twice with water, dried and concentrated to dryness. Chromatography of the residue afforded syrupy title compound 3 (R=Et) (0.55 g).

Example 5.3

(1S)-1-(3-Amino-2-cyanopyrrol-4-yl)-N-tert-butoxycarbonyl-1,4-dideoxy-5-ethylthio-1,4-imino-2,3-O-isopropylidene-D-ribitol (4, R=Et)

Ethyl formate (1.1 mL) was added to a solution of 3 (R=Et) (0.48 g) in THF (10 mL) followed by sodium hydride (0.22 g, 60% dispersion). The mixture was stirred for 2 h, then acetic acid (0.6 mL) was added and the solution was partitioned between chloroform and water, the organic phase was dried and concentrated to dryness. A solution of the residue in methanol (15 mL) was treated with sodium acetate (1.1 g), and aminoacetonitrile hydrochloride (0.62 g) and the mixture was stirred for 16 h and then was heated under reflux for 0.5 h. The resulting mixture was partitioned between chloroform and water, the organic phase was dried and concentrated to dryness. A solution of the residue in dichloromethane (20 mL) was treated with DBU (1.24 mL) and methyl chloroformate (0.3 mL) and the solution was stirred for 16 h, then was washed with dil HCl and aq NaHCO$_3$, dried and concentrated to dryness. The residue in methanol (10 mL) was treated with triethylamine (1 mL). After 2 h at room temperature the solution was concentrated to dryness. Chromatography of the residue gave syrupy 4 (R=Et) (0.49 g).

Example 5.4

(1S)-1-(9-Deazaadenin-9-yl)-1,4-dideoxy-5-ethylthio-1,4-imino-D-ribitol

A solution of the product from Example 5.3 in ethanol (15 mL) containing formamidine acetate (0.25 g) was heated under reflux for 3 h and then concentrated to dryness. Chromatography afforded 0.47 g of material which was dissolved in methanol (10 mL) and 4M HCl (10 mL). After 6 h at room temperature the solution was concentrated to dryness. Trituration with ethanol or propan-2-ol gave the title compound as a bis hydrochloride salt, white solid (0.275 g) with m.p. 204–212° C. (dec).

The following compounds were prepared by the same sequence of reactions as above except that the appropriate thiol replaced ethanethiol.

(1S)-1-(9-Deazaadenin-9-yl)-1,4-dideoxy-1,4-imino-5-phenylthio-D-ribitol bis hydrochloride. M.p. 180–182° C.; $^{13}$C NMR (D$_2$O) δ 149.1, 143.4, 139.5, 133.0, 132.9, 130.9, 130.0, 128.1, 113.0, 105.9, 73.2, 72.6, 63.8, 56.7, 33.8.

(1S)-1-(9-Deazaadenin-9-yl)-5-benzylthio-1,4-dideoxy-1,4-imino-D-ribitol bis hydrochloride. $^{13}$C NMR (D$_2$O) δ 149.2, 143.5, 138.1, 133.0, 129.4, 128.0, 113.0, 105.9, 73.2, 72.6, 63.9, 56.6, 35.6, 30.8.

(1S)-1-(9-Deazaadenin-9-yl)-1,4-dideoxy-5-(2-hydroxyethyl)thio-1,4-imino-D-ribitol bis hydrochloride. $^{13}$C NMR (D$_2$O) δ 149.4, 143.6, 139.4, 133.0, 113.1, 105.8, 73.2, 72.6, 64.3, 60.8, 56.5, 34.2, 31.7.

(1S)-1-(9-Deazaadenin-9-yl)-1,4-dideoxy-1,4-imino-5-(4-methylphenyl)thio-D-ribitol bis hydrochloride. $^{13}$C NMR (D$_2$O) δ 149.0, 143.3, 139.6, 139.0, 133.0, 131.6, 130.6, 129.0, 113.0, 105.9, 73.3, 72.6, 63.9, 56.8, 34.4, 20.5.

(1S)-1-(9-Deazaadenin-9-yl)-1,4-dideoxy-1,4-imino-5-(3-methylphenyl)thio-D-ribitol bis hydrochloride. $^{13}$C NMR (D$_2$O) δ 149.00, 143.3, 140.4, 139.6, 133.0, 132.7, 131.2, 129.8, 128.8, 127.8, 113.0, 105.9, 73.3, 72.6, 63.8, 56.7, 33.8, 20.8.

(1S)-1-(9-Deazaadenin-9-yl)-5-(4-chlorophenyl)thio-1,4-dideoxy-1,4-imino-D-ribitol bis hydrochloride. $^{13}$C NMR (D$_2$O) δ 149.0, 143.3, 139.7, 133.6, 133.0, 132.4, 131.6, 129.8, 113.0, 105.9, 73.3, 72.6, 63.6, 56.7, 34.0.

(1S)-1-(9-Deazaadenin-9-yl)-5-(3-chlorophenyl)thio-1,4-dideoxy-1,4-imino-D-ribitol bis hydrochloride. $^{13}$C NMR (D$_2$O) δ 148.9, 143.3, 139.6, 135.1, 134.8, 133.1, 131.1, 129.9, 128.8, 128.0, 113.0, 105.9, 73.3, 72.6, 63.6, 56.8, 33.6.

(1S)-1-(9-Deazaadenin-9-yl)-1,4-dideoxy-5-(4-fluorophenyl)thio-1,4-imino-D-ribitol bis hydrochloride. $^{13}$C NMR (D$_2$O) δ 162.8 (d, $J_{C,F}$=245 Hz), 149.1, 143.4, 139.6, 134.1 (d, $J_{C,F}$=8.4 Hz), 133.0, 127.9, 116.9 (d, $J_{C,F}$=22 Hz), 113.0, 105.8, 73.2, 72.5, 63.7, 56.6, 35.0.

(1S)-1-(9-Deazaadenin-9-yl)-1,4-dideoxy-1,4-imino-5-(1-naphthyl)thio-D-ribitol bis hydrochloride. $^{13}$C NMR (D$_2$O) δ 142.7, 132.9, 130.3, 130.1, 129.2, 127.6, 127.3, 126.4, 124.6, 73.2, 72.8, 63.9, 57.2, 33.5.

Example 5.5

(1S)-1-(9-Deazaadenin-9-yl)-1,4-dideoxy-5-(2-fluoroethyl)thio-1,4-imino-D-ribitol A solution of N-tert-butoxycarbonyl-5-(2-hydroxyethyl)thio-3,6-imino-4,5-O-isopropylidene-2,3,6-trideoxy-D-allo-heptononitrile (3, R=CH$_2$CH$_2$OH) (1.0 g) in dry chloroform (10 mL) was treated with DAST (0.71 mL) and the solution was allowed to stand for 16 h, then was washed with water, aq NaHCO₃, dried and concentrated to dryness. Chromatography afforded syrupy N-tert-butoxycarbonyl-5-(2-fluoroethyl)thio-3,6-imino-4,5-O-isopropylidene-2,3,6-trideoxy-D-allo-heptononitrile (3, R=CH₂CH₂F) (0.558 9). This material was converted into the title compound by the same sequence of reactions as above in Examples 5.3 and 5.4 to give a solid bis-hydrochloride salt (0.307 g). ¹³C NMR (D₂O) δ 149.4, 143.6, 139.5, 133.1, 113.1, 105.8, 84.2 (d, $J_{C,F}$=164 Hz), 73.2, 72.6, 64.2, 56.5, 31.9, 31.9 (d, $J_{C,F}$=20 Hz).

Example 6

Preparation of (1S)-1-(9-deazaadenin-9-yl)-1,4,5-trideoxy-5-C-ethyl-1,4-imino-D-ribitol (Scheme 5)

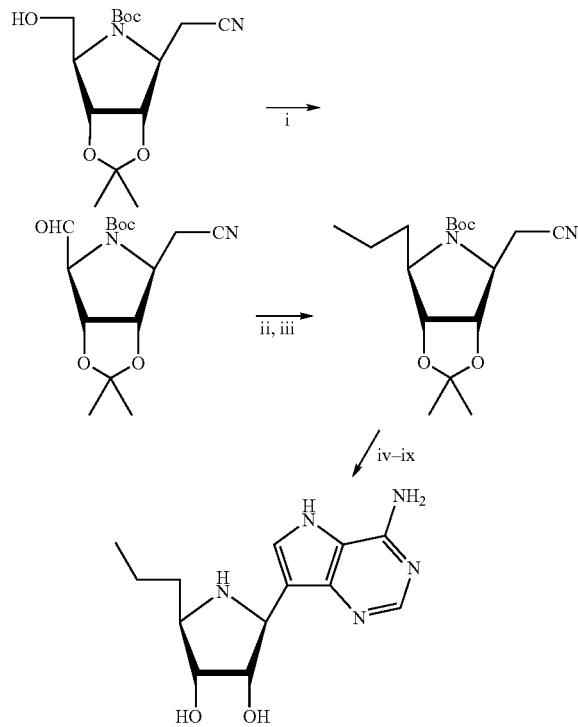

Example 6.1

N-Tert-butoxycarbonyl-3,6-imino-4,5-O-isopropylidene-2,3,6,7,8,9-hexadeoxy-D-allo-nonononitrile Dess-Martin periodinane (1.42 g) was added to a solution of N-tert-butoxycarbonyl-3,6-imino-4,5-O-isopropylidene-2,3,6-trideoxy-D-allo-heptononitrile (Example 5.2, Compound (2) of Scheme 4) (0.7 g) in dichloromethane (20 mL) and the resulting mixture was stirred for 1 h. After concentrating to dryness, ether (20 mL) was added to the residue and the mixture was washed twice with 10% aq Na₂S₂O₃/sat. aq NaHCO₃ (1:1 v/v), dried and concentrated to dryness. A solution of this residue in THF (8 mL) was added to the red solution resulting from addition of n-butyllithium (3.4 mL, 1.6 M) to a suspension of ethyltriphenylphosphonium iodode (2.44 g) in THF (25 mL). After 0.5 h, the mixture was diluted with petroleum ether (100 mL) and washed with water, dried and concentrated to dryness. Chromatography afforded a syrup (0.34 g). This material in ethanol (10 mL) containing 10% Pd/C (0.05 g) was stirred in an atmosphere of hydrogen for 2.5 h, then the solids and solvent were removed. Chromatography afforded syrupy title compound (0.282 g).

Example 6.2

(1S)-1-(9-Deazaadenin-9-yl)-1,4,5-trideoxy-5-ethyl-1,4-imino-D-ribitol bis hydrochloride The material from example 6.1 was treated with the same sequence of reactions as in examples 5.3 and 5.4 above to give title compound as a white solid bis-hydrochloride salt (0.095 g) with m.p. 206–215° C. ¹³C NMR (D₂O) δ 149.7, 143.8, 138.8, 132.9, 113.1, 105.6, 73.0, 72.9, 65.1, 55.9, 32.8, 19.4, 13.2.

Example 7

Enzyme Inhibition Results

Enzyme assays were conducted to assess the effectiveness of selected compounds of the invention as inhibitors of MTAP and MTAN. The results are collected in Tables 1 and 2 and shown in FIG. 1.

Enzymes.—The human MTAP protein was cloned into pQE32 expression vector and transformed into E. coli. Induction cultures containing 1 L (25 mg/L) and 50 µg/mL ampicillin were inoculated with 1 mL overnight grown starter-culture and incubated at 37° C. When the cultures reached an OD of ≈0.6 they were induced with 1.5 mM IPTG for 6 to 8 hours. Cells were harvested by centrifugation at 5000 rpm for 30 min, and subsequently resuspended in a buffer (20 mM imidazole, 300 mM NaCl, 0.2 mM phenylmethylsulfonyl fluoride (PMSF), 100 mM Tris, pH 8.0) containing a small amount of lysozyme to weaken the cell membrane. Cells were lysed with a French press. The insoluble material was removed by high-speed centrifugation. The cell extract was further clarified with 35% ammonium sulfate precipitation followed by high-speed centrifugation. The clarified cell extract was then applied to a 5 mL Ni-NTA column that had previously been equilibrated with the binding buffer. Further chromatographic steps were carried out by FPLC. The column was washed with 10 volumes of 50 mM imidazole, 300 mM NaCl, and 100 mM Tris, pH 8.0, and the protein was eluted with a buffer containing a 50–250 mM gradient of imidazole, 300 mM NaCl, 1 M Tris, pH 8.0. The purity of the protein was verified by running polyacrylamide gel followed by Coomassie staining. The protein was subsequently dialyzed in 50 mM NaCl, 2 mM dithiothreitol (DTT) and 50 mM Tris, pH 7.4, and was concentrated to 10 mg/mL. The purified protein was stored at −80° C. in 100 µL to 150 µL aliquots.

Inhibitors.—Inhibitor concentrations were determined by the UV absorbance spectrum using the published millimolar extinction coefficients for 9-dazadenine of 8.5 at 275 nm at pH 7.0.

Assays.—The direct spectrophotometric assay for the conversion of MTA into adenine was measured as the decrease in absorbance at 274 nm. At 274 nm, Δε between MTA and adenine is at a maximum and produces a spectral change of 1.6 absorbance units/cm/mM (DeWolf, W. E. Jr., Fullin, F. A., and Schramm, V. L. (1979) J. Biol. Chem. 254, 10868–10875)

Slow-Onset Inhibition and Inhibition Constants.—The kinetics for slow onset inhibition and the $K_i$ measurement was carried out by adding a known concentration of enzyme (1–5 nM) to a reaction mixture containing a substrate concentration of 200 µM. This concentration corresponds to an OD of 0.7–1.1 at 274 nM. The formation of product was monitored as a decrease in absorbance at 274 nm. Conditions for $K_i^*$ determination used high concentrations of substrate. Two controls, one having no inhibitor and the other no enzyme were included in the experiment. The $K_i$ values MTAP for the various compounds were calculated by fitting in the ratio of initial rates in the presence of inhibitor to without any inhibitor versus the inhibitor concentration, for the known $K_m$ and substrate concentration into the following expression.

$$\frac{V_o'}{V_o} = \frac{K_m + [S]}{K_m + [S] + K_m \frac{[I]}{K_i}}$$

Where $V_o'$ is the rate in the presence of inhibitor $V_o$ rate in the absence of inhibitor

[I] inhibitor concentration

And [S] is the substrate concentration

And the $K_i^*$ was calculated by fitting to the following expression $$\frac{V_s'}{V_s} = \frac{K_m + [S]}{K_m + [S] + K_m \frac{[I]}{K_i^*}}$$

Where $V_s'$ is the steady-state rate following attainment of equilibrium in the presence inhibitor, and $V_s$ is the steady-state rate in the control having no inhibitor. Both these equations are valid for competitive type inhibition.

Inhibitor Release Studies.—The enzymes and the inhibitor were preincubated at the indicated concentrations for 3–4 h in 50 mM potassium phosphate, pH 7.4. At the indicated times the samples were diluted by the factors of 1:10000 to 1:1000000 into assay mixtures, and the rate of product formation was determined as a function of time. Control incubations had all components but inhibitors. To accommodate slow dissociation of enzyme and inhibitor, very high concentration of substrates and low concentration of enzymes were used.

Competitive Inhibition.—The nature of inhibition is established by constructing a four by four-double reciprocal plot. The substrate concentrations were chosen such that they were both below and above the $K_m$ value of the enzyme, and the inhibitor concentrations were around the dissociation constant of the enzyme. The reaction is started by adding the enzyme solution to each of the 16 reaction mixtures containing above-mentioned substrate and inhibitor concentrations. The initial rates were calculated. The reciprocal of initial rates were plotted as a function of inverse of substrate concentration to get Lineweaver-Burke plot. For competitive inhibition the point of intersection with the y-axis give us $1/V_{max}$. The slope of the curve is $\alpha$ $K_m/V_{max}$, where $\alpha=1+[I]/K_i$.

Example 8

Demonstration of Radiation Sensitizing Effect of 5'-Methylthio-ImmA

Lewis lung carcinoma cells ($1\times10^6$) were plated and allowed to adhere overnight in 2 mL of DMEL medium substituted with 10% fetal bovine serum, 1% Pen-Strep, 2.5% Na-Pyruvate, 1% non-essential amino acids in 6 well plates. 50 µM MTA, 50 µM MTA+2 µM 5'-methylthio-ImmA or 2 µM 5'-methylthio-ImmA was then added in 1 mL of the same medium as indicated. Control wells were treated with medium without any additions. This treatment was allowed to continue for 6 hours. In each experiment one set of treated cells were subjected to 10 Gy of X-ray irradiation and a control set received no irridation. Both irradiated and unirradiated cells were then cultured for another 48 hours in the presence of MTA±5'-methylthio-ImmA. Manual counting of living and dead cells was done by Trypan Blue dye exclusion following 48 hrs of growth. (Approximate doubling time for Lewis Lung cells was 24 hours.)

The results are shown in FIG. 2, and indicate:

Control—irradiation reduces cell numbers by 50% in the absence of additives.

MTA at 50 µM reduces growth of cells, but slightly protects from irradiation damage.

5'-methylthio-ImmA at 2 µM acts in a similar manner to 50 µM MTA.

5'-methylthio-ImmA+MTA is an irradiation sensitizer, lowering cancer cell number following irradiation.

Example 9

Demonstration of Tissue Availability of 5'-Methylthio-ImmA in Mice

5'-Methylthio-Immucillin-A (5'-methylthio-ImmA) (10 micromoles) was administered to mice orally, by interperitoneal injection or by intravenous injection. Following 30 to 60 min, blood was collected or mice were sacrificed and the liver removed for tissue analysis. MTAP activity in mouse blood was measured by the conversion of radioactive MTA to radioactive 5-methylthio-α-D-ribose 1-phosphate (MTR-1P). The assay mixture contained 50 mM phosphate buffer, 1 mM dithiothreitol, 26 µM [5'-$^{14}$C]MTA with specific radioactivity of 2 µCi/µmole, 0.5% triton X-100, and the desired amount of tissue sample, in a total volume of 100 µL. Reactions were stopped at various times by the addition of perchloric acid to decrease the pH to 2.0. The protein precipitate was removed by centrifugation, and the supernatant was neutralized to near pH 7 before being placed on a charcoal column. The column was eluted with buffer near pH 7. The product MTR-1P elutes, while unreacted [5'-$^{14}$C] MTA remains on the column. The amount of MTAP activity from control and treated mice is compared.

Figure 3:
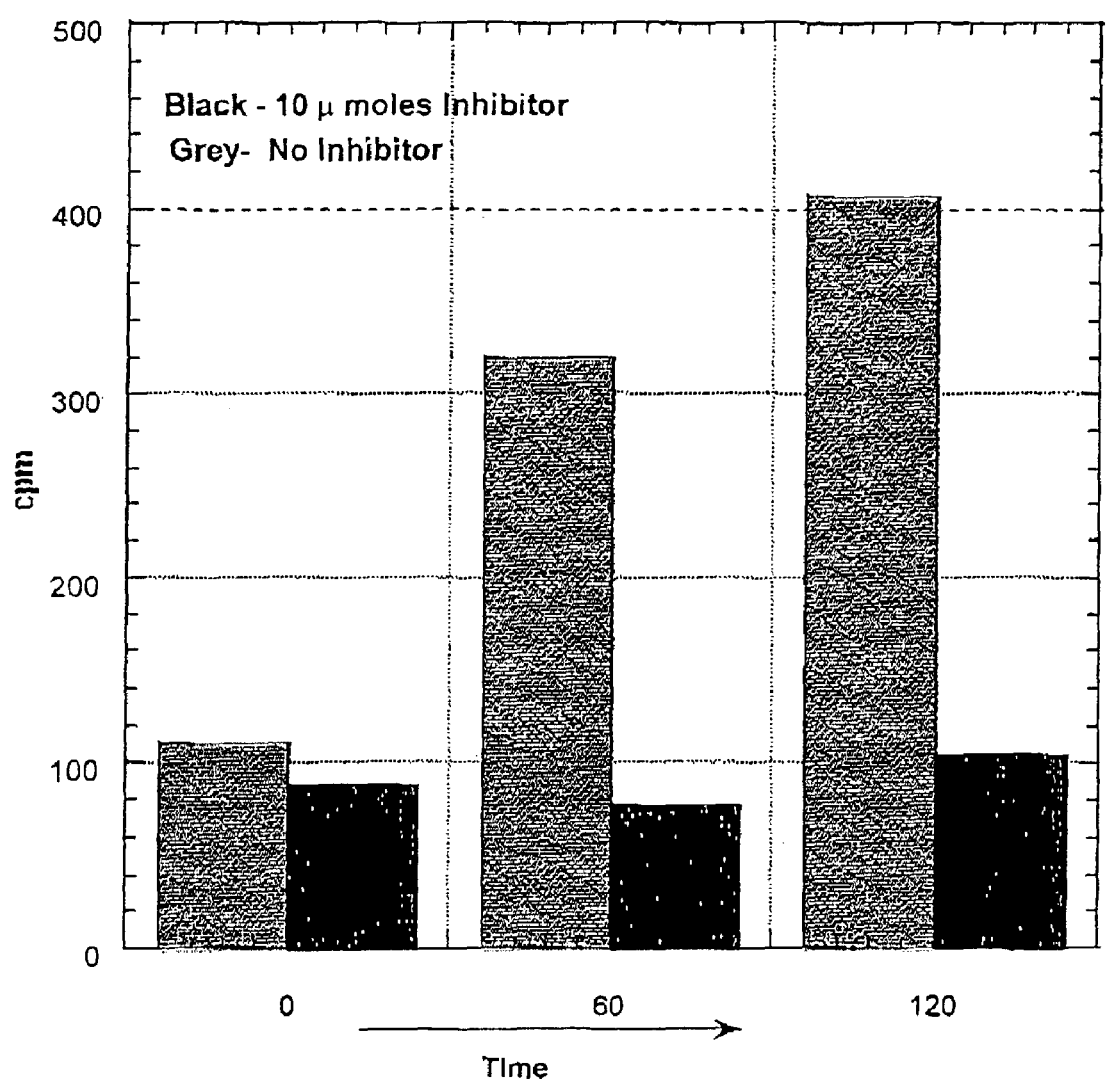
FIG. 3 shows the effect of 5'-methylthio-ImmA on MTAP activity in mouse blood.

FIG. 3 shows the effect of 5'-methylthio-ImmA on MTAP activity in mouse blood.

Liver protein extracts from control mice converted MTA to products at a rate of 1.0 nMole/min/mg of liver protein extract. Following oral administration of 10 µmoles of 5'-methylthio-ImmA, the MTAP in extracts of liver converted MTA to products at a rate of 0.09 nMole/min/mg of liver protein extract treatment, corresponding to 90% inhibition. Therefore 5'-methylthio-ImmA is orally available to the MTAP present inside tissues. In a similar experiment where 5'-methylthio-ImmA was provided by intravenous injection, there was no detectable MTAP activity in liver extracts, indicating that >95% of inhibiton occurred. To estimate the sensitivity of the liver tissue MTAP to the administration of 5'-methylthio-ImmA, mice were injected by intraperitoneal injection with 0.1 or 1.0 micromoles of MT-Imm-A. In this protocol injection of 0.1 micromole of 5'-methylthio-ImmA reduced the MTAP activity of liver extract by 70% and injection of 1.0 micromole of 5'-methylthio-ImmA reduced the MTAP activity of liver extract by 77%. Interperitoneal injection of 10 micromoles of 5'-methylthio-ImmA also inhibited the activity of MTAP found in mouse blood. Blood sampled 30 min following 5'-methylthio-ImmA injection was >90% inhibited compared to control blood.

Figure 4:
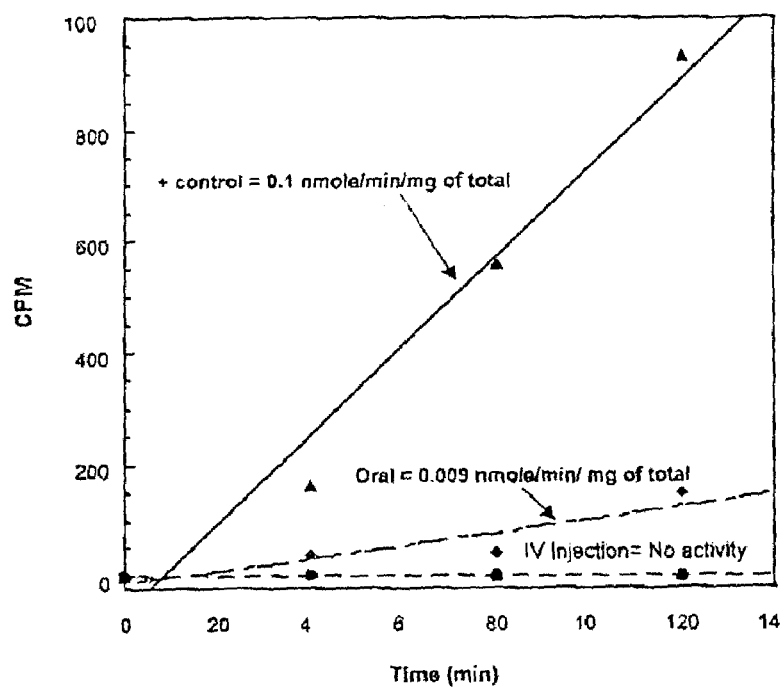
FIG. 4 shows inhibition of mouse liver MTAP by 5'-methylthio-ImmA.

FIG. 4 shows inhibition of mouse liver MTAP by 5'-methylthio-ImmA.

Although the invention has been described by way of examples, it should be appreciated the variations or modifications may be made without departing from the scope of the invention. Furthermore, when known equivalents exist to specific features, such equivalents are incorporated as if specifically referred to in the specification.

INDUSTRIAL APPLICABILITY

The present invention relates to compounds that are inhibitors of MTAP and MTAN. The compounds are therefore expected to be useful in the treatment of diseases in which the inhibition of MTAP and MTAN is desirable. Such diseases include cancer, bacterial infections and protozoan parasitic infections.

The invention claimed is:

1. A compound of the formula (I):

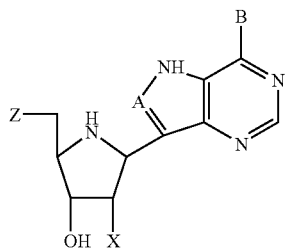

(I)

wherein:
A is selected from CH and CR,
where R is selected from halogen, alkyl, aralkyl, aryl, OH, $NH_2$, $NHR^1$, $NR^1R^2$ and $SR^3$,
where $R^1$, $R^2$ and $R^3$ are each alkyl, aralkyl or aryl groups;
B is selected from $NH_2$ and $NHR^4$,
where $R^4$ is an alkyl, aralkyl or aryl group;
X is selected from H, OH and halogen; and
Z is SQ, where Q is a $C_2$–$C_5$ alkyl group; a $C_2$–$C_5$ alkyl group substituted with a halogen; a phenyl group; or a phenyl group substituted with a halogen or a methyl;
or a tautomer thereof; or a pharmaceutically acceptable salt thereof;
with the proviso that the stereochemistry of the aza-sugar moiety is D-ribo or 2'-deoxy-D-erythro-.

2. A compound as claimed in claim 1, where A is CH.
3. A compound as claimed in claim 1, where B is $NH_2$.
4. A compound as claimed in claim 1, where Q is $C_2$–$C_5$ alkyl.
5. A compound as claimed in claim 1 where X is OH.

6. A compound as claimed in claim 1, where Q is selected from phenyl, 3-chlorophenyl, 4-chlorophenyl, 4-fluorophenyl, 3-methylphenyl, and 4-methylphenyl.

7. A compound as claimed in claim 1, selected from:
(1S)-1-(9-Deazaadenin-9-yl)-1,4-dideoxy-5-ethylthio-1,4-imino-D-ribitol;
(1S)-1-(9-Deazaadenin-9-yl)-1,4-dideoxy-1,4-imino-5-phenylthio-D-ribitol;
(1S)-1-(9-Deazaadenin-9-yl)-1,4-dideoxy-1,4-imino-5-(4-methylphenyl)thio-D-ribitol;
(1S)-1-(9-Deazaadenin-9-yl)-1,4-dideoxy-1,4-imino-5-(3-methylphenyl)thio-D-ribitol;
(1S)-1-(9-Deazaadenin-9-yl)-5-(4-chlorophenyl)thio-1,4-dideoxy-1,4-imino-D-ribitol;
(1S)-1-(9-Deazaadenin-9-yl)-5-(3-chlorophenyl)thio-1,4-dideoxy-1,4-imino-D-ribitol;
(1S)-1-(9-Deazaadenin-9-yl)-1,4-dideoxy-5-(4-fluorophenyl)thio-1,4-imino-D-ribitol; and
(1S)-1-(9-Deazaadenin-9-yl)-1,4-dideoxy-5-(2-fluoroethyl)thio-1,4-imino-D-ribitol;
or a tautomer thereof; or a pharmaceutically acceptable salt thereof.

8. A pharmaceutical composition comprising a pharmaceutically effective amount of a compound as claimed in claim 1 and a carrier.

9. A compound of the formula (I):

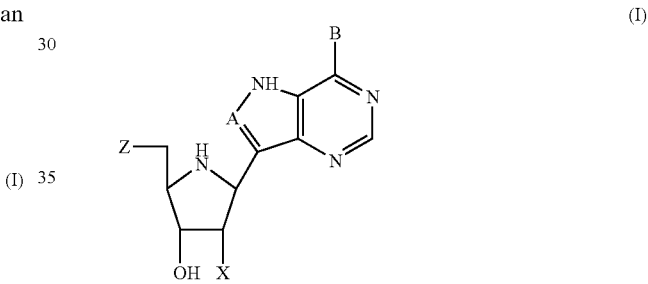

(I)

wherein:
A is selected from CH and CR,
where R is selected from halogen, alkyl, aralkyl, aryl, OH, $NH_2$, $NHR^1$, $NR^1R^2$ and $SR^3$,
where $R^1$, $R^2$ and $R^3$ are each alkyl, aralkyl or aryl groups;
B is selected from $NH_2$ and $NHR^4$,
where $R^4$ is an alkyl, aralkyl or aryl group;
X is selected from H, OH and halogen; and
Z is Q, where Q is an alkyl, aralkyl or aryl group;
or a tautomer thereof; or a pharmaceutically acceptable salt thereof;
with the proviso that the stereochemistry of the aza-sugar moiety is D-ribo or 2'-deoxy-D-erythro-.

10. A compound as claimed in claim 9, where A is CH.
11. A compound as claimed in claim 9, where B is $NH_2$.
12. A compound as claimed in claim 9, where X is OH.
13. A compound as claimed in claim 9, selected from:
(1S)-1-(9-deazaadenin-9-yl)-1,4,5-trideoxy-1,4-imino-D-ribitol;
(1S)-1-(9-Deazaadenin-9-yl)-1,4,5-trideoxy-5-ethyl-1,4-imino-D-ribitol;
or a tautomer thereof; or a pharmaceutically acceptable salt thereof.

14. A pharmaceutical composition comprising a pharmaceutically effective amount of a compound as claimed in claim 9 and a carrier.

15. A compound as claimed in claim 1, where Q is a $C_2$–$C_5$ alkyl group substituted with a fluoro, or a phenyl group substituted with a chloro or a fluoro.

16. A compound selected from:
- (1S)-1-(9-deazaadenin-9-yl)-1,4,5-trideoxy-1,4-imino-D-ribitol;
- (1S)-1-(9-Deazaadenin-9-yl)-5-benzylthio-1,4-dideoxy-1,4-imino-D-ribitol;
- (1S)-1-(9-Deazaadenin-9-yl)-1,4-dideoxy-5-(2-hydroxyethyl)thio-1,4-imino-D-ribitol;
- (1S)-1-(9-Deazaadenin-9-yl)-1,4-dideoxy-1,4-imino-5-(1-naphthyl)thio-D-ribitol;
- (1S)-1-(9-Deazaadenin-9-yl)-1,4,5-trideoxy-5-ethyl-1,4-imino-D-ribitol; and
- (1S)-1-(9-deazaadenin-9-yl)-1,4-dideoxy-1,4-imino-5-O-methyl-D-ribitol;

or a tautomer thereof; or a pharmaceutically acceptable salt thereof.

\* \* \* \* \*